(12) United States Patent
Kar et al.

(10) Patent No.: US 11,326,139 B2
(45) Date of Patent: May 10, 2022

(54) AEROBIC FERMENTATION SYSTEMS AND METHODS

(71) Applicant: Dow Global Technologies LLC, Midland, MI (US)

(72) Inventors: Kishore K. Kar, Midland, MI (US); Suraj S. Deshpande, Midland, MI (US); James J. Pressler, Midland, MI (US); Bianca Fernandes Martins, Sao Paulo (BR); Iris Raquel Maia Tebeka, Freeport, TX (US); Devon C. Rosenfeld, Freeport, TX (US); John Richard Biggs, Sao Paulo (BR)

(73) Assignee: Dow Global Technologies LLC, Midland, MI (US)

( * ) Notice: Subject to any disclaimer, the term of this patent is extended or adjusted under 35 U.S.C. 154(b) by 185 days.

(21) Appl. No.: 16/486,278

(22) PCT Filed: Mar. 8, 2018

(86) PCT No.: PCT/US2018/021518
§ 371 (c)(1),
(2) Date: Aug. 15, 2019

(87) PCT Pub. No.: WO2018/165411
PCT Pub. Date: Sep. 13, 2018

(65) Prior Publication Data
US 2019/0367862 A1     Dec. 5, 2019

Related U.S. Application Data

(60) Provisional application No. 62/469,796, filed on Mar. 10, 2017.

(51) Int. Cl.
*C12M 1/00* (2006.01)
*C12M 1/02* (2006.01)
*C12M 1/12* (2006.01)

(52) U.S. Cl.
CPC .............. *C12M 29/24* (2013.01); *C12M 1/00* (2013.01); *C12M 27/00* (2013.01); *C12M 29/06* (2013.01);
(Continued)

(58) Field of Classification Search
CPC ........ C12M 29/24; C12M 1/00; C12M 27/00; C12M 29/06; C12M 29/18; C12M 29/26; C12M 37/00; C12M 41/18
See application file for complete search history.

(56) References Cited

U.S. PATENT DOCUMENTS 4,070,279 A * 1/1978 Armstrong ................ C02F 3/20
                                                          210/629
4,329,433 A * 5/1982 Seebeck .................... C12P 7/06
                                                          435/162
(Continued)

FOREIGN PATENT DOCUMENTS

CN    2102931 U    4/1992
CN    1099795 A    3/1995
(Continued)

OTHER PUBLICATIONS

Deckwer et al., "Mixing and mass transfer in tall bubble columns," Chemical Engineering Science, vol. 29, No. 11, 1974.
(Continued)

*Primary Examiner* — William H. Beisner
*Assistant Examiner* — Danielle B Henkel
(74) *Attorney, Agent, or Firm* — Dinsmore & Shohl LLP

(57) ABSTRACT

A system for aerobic fermentation includes a vessel, an aeration system including a gas sparger fluidly coupled to the vessel to introduce a compressed gas to an internal volume of the vessel, and a recirculation loop fluidly coupled to an outlet of the vessel. The recirculation loop includes an eductor fluidly coupled to an oxygen-containing
(Continued)

gas source, a static mixer downstream of the eductor, a heat exchanger downstream of the eductor, and a distributor downstream of the heat exchanger. The distributor is fluidly coupled to the vessel. The aeration system provides mixing and oxygen mass transfer to the fermentation composition in the vessel. The fermentation composition passes through the eductor, static mixer, heat exchanger, and distributor of the recirculation loop, and back into the vessel. Oxygen is transferred from an oxygen containing gas to the fermentation composition and heat is removed from the fermentation composition in the recirculation loop.

17 Claims, 11 Drawing Sheets

(52) U.S. Cl.
CPC ............ *C12M 29/18* (2013.01); *C12M 29/26* (2013.01); *C12M 37/00* (2013.01); *C12M 41/18* (2013.01)

(56) References Cited

U.S. PATENT DOCUMENTS

| | | | | |
|---|---|---|---|---|
| 4,935,348 | A * | 6/1990 | Gerard oosterhuis | ...................... B01J 19/1837 435/41 |
| 5,837,529 | A | 11/1998 | Wan et al. | |
| 6,250,796 | B1 | 6/2001 | Huang | |
| 8,178,330 | B2 | 5/2012 | Trevethick et al. | |
| 8,257,961 | B2 * | 9/2012 | Brahmbhatt | ........ B01F 3/04262 435/283.1 |
| 2002/0115132 | A1 * | 8/2002 | Ho | ........................... C01B 32/50 435/41 |
| 2009/0107913 | A1 * | 4/2009 | Johnson | .................. C12M 47/18 210/604 |
| 2015/0259639 | A1 * | 9/2015 | Silverman | .............. C12M 23/06 435/123 |
| 2016/0115505 | A1 * | 4/2016 | Trevethick | ................ C12P 7/54 435/140 |
| 2017/0362562 | A1 * | 12/2017 | Nguyen | .................... C12N 1/30 |

FOREIGN PATENT DOCUMENTS

| | | |
|---|---|---|
| CN | 2205388 Y | 8/1995 |
| EP | 3031896 A1 | 6/2016 |
| WO | 0046354 A1 | 8/2000 |
| WO | 03025158 A1 | 3/2003 |
| WO | 2016092073 A1 | 6/2016 |

OTHER PUBLICATIONS

Krishna et al., "Gas holdup in bubble column reactors operating in the churn-turbulent flow regime," AIChE Journal, vol. 42, 1996.
Shaikh et al., "Scale-up of bubble column reactors: A review of current state-of-the-art," I&EC, vol. 52, 2013.
Chern et al., "Oxygen transfer rate in a coarse bubble diffused aeration system," Ind. Eng. Chem. Res. , vol. 42, 2003.
Popel et al., "Modelling of oxygen transfer in deep diffused aeration tanks and comparison with full scale plant data," Water Science Technology, vol. 30, No. 4, 1994.
International Search Report and Written Opinion pertaining to PCT/US2018/021518, dated Jun. 19, 2018.
"Aeration Products for Energy-Efficient Biological Treament," Xylem, Inc. (2012).
Hur, D., "A computer program for optimal aeration system design for activated sludge treatment plants", University of California at Los Angeles, 1994.
Heyouni et al., "Hydrodynamics and mass transfer in gas-liquid flow through static mixers," Chemical Engineering Science, vol. 57, pp. 3325-3333, 2002.
Benz, Gregory T., "Large Scale Microbial Production of Advanced Biofuels: How big can we go?", SIMB Poster, 2016.
Turunen et al., "Mass transfer in tubular reactors equipped with static mixers," Chemical Engineering Science, vol. 19, No. 24B, pp. 5257-5269, 1994.
Schneider, "Static mixers as gas/liquid reactors," Institution of Chemical Engineers Symposium Series, 1990.
Visser et al., "Three-dimensional numerical simulation of flow and heat transfer in the Sulzer SMX static mixer," Chemical Engineering Science, vol. 54, No. 13, pp. 2491-2500, 1999.
Levy et al., "Biochemical Engineering Approaches to the Challenges of Producing Pure Plasmid DNA", TIBTECH, 2000, vol. 18, 296-305.
Shah, et al., "Design Parameters Estimations for Bubble Column Reactors", AIChE Journal (vol. 28, No. 3), May 1982, pp. 353-379.
Wilkinson, et al., "Design Parameters Estimation for Scale-Up of High-Pressure Bubble Columns", AIChE Journal (vol. 38, No. 4), Apr. 1992, pp. 544-554.

* cited by examiner

AEROBIC FERMENTATION SYSTEMS AND METHODS

CROSS REFERENCE TO RELATED APPLICATION

This application claims priority to U.S. Provisional Patent Application Ser. No. 62/469,796 filed Mar. 10, 2017, which is incorporated by reference herein in its entirety.

TECHNICAL FIELD

Embodiments of the present disclosure generally relate to aerobic fermentation systems and methods, in particular aerobic fermentation systems for conducting aerobic fermentation at greater-production rates in large volume vessels.

BACKGROUND

Fermentation may be used to convert organic materials into one or more compounds through microbial metabolism by microorganisms. These compounds are recovered from the fermentation broth as commercial products or raw materials or intermediates for further processing. Conducting fermentation processes in the presence of oxygen to create aerobic conditions may be referred to as aerobic fermentation. Success of aerobic fermentation processes depend upon the ability to oxygenate the fermentation broth. In particular, a mass transfer rate of oxygen into the fermentation broth should be maintained at least equal to the minimum uptake rate of oxygen due to a given microbial metabolism. This ensures that the oxygen consumed by microbial metabolism is sufficiently replenished in the fermentation broth and prevents the fermentation process from transitioning to anaerobic fermentation, and/or oxygen starvation, which may lead to changes in the metabolic pathway of the microorganisms, rate of metabolism, or death of the microorganisms. Aerobic fermentation generates heat which must be removed from the fermentation broth.

Many aerobic fermentation processes employ stirred vessels with air sparging to maintain the oxygenation of the fermentation broth. However, motorized agitation becomes infeasible at fermentation capacities, typically larger than 500 m$^3$. At these volumes, the motorized agitation sufficient to maintain oxygenation of the fermentation broth can be prohibitively expensive. Also, the resulting mechanical stresses on the fermentation tanks to which the motors are coupled can challenge the structural integrity of the fermentation vessel. The capacity of an agitated aerobic fermentation system is, thus, constrained by (i) cost and availability of the drive, as well as (ii) mechanical strength of the fermenter.

SUMMARY

Accordingly, ongoing needs exist for improved systems and methods for conducting aerobic fermentations at greater production capacities. Embodiments of the present disclosure are directed to aerobic fermentation systems and methods for conducting aerobic fermentation at greater production capacities using large volume vessels.

According to an embodiment, a system for aerobic fermentation includes a vessel, an aeration system comprising a gas sparger fluidly coupled to the vessel and positioned to introduce a compressed gas to an internal volume of the vessel, and a recirculation loop fluidly coupled to an outlet of the vessel. The recirculation loop comprises at least one eductor fluidly coupled to an oxygen-containing gas source, at least one static mixer downstream of the at least one eductor, at least one heat exchanger downstream of the at least one eductor, and at least one distributor downstream of the at least one static mixer and the at least one heat exchanger. The at least one distributor is fluidly coupled to the internal volume of the vessel. When a fermentation composition is introduced to the vessel, the gas sparger and the recirculation loop provide mixing to the fermentation composition, and a stream of the fermentation composition passes from the vessel into the recirculation loop, through the at least one educator, the at least one static mixer, and the at least one heat exchanger of the recirculation loop, and passes out of the at least one distributor back into the internal volume of the vessel.

In another embodiment, a method for conducting aerobic fermentation includes introducing a fermentation composition to a vessel, sparging a first oxygen-containing gas stream into the fermentation composition, and passing a stream of the fermentation composition into a recirculation loop comprising at least one eductor, at least one static mixer downstream of the at least one eductor, and at least one heat exchanger downstream of the at least one eductor. The method further includes educting a second oxygen-containing gas stream into the stream of the fermentation composition with the at least one eductor to produce a combined stream comprising a liquid phase and a gas phase. The liquid phase comprises the fermentation composition, and the gas phase comprises the second oxygen-containing gas. The method further includes transferring oxygen from the gas phase to the liquid phase using the at least one static mixer to produce an oxygenated fermentation composition in the liquid phase, removing heat from the oxygenated fermentation composition using the at least one heat exchanger, and passing the oxygenated fermentation composition from the recirculation loop back to the vessel.

Additional features and advantages of the described embodiments will be set forth in the detailed description which follows, and in part will be readily apparent to those skilled in the art from that description or recognized by practicing the described embodiments, including the detailed description which follows, the claims, as well as the appended drawings.

BRIEF DESCRIPTION OF THE DRAWINGS

The following detailed description of specific embodiments of the present disclosure can be best understood when read in conjunction with the following drawings, where like structure is indicated with like reference numerals and in which.

Figure 1:
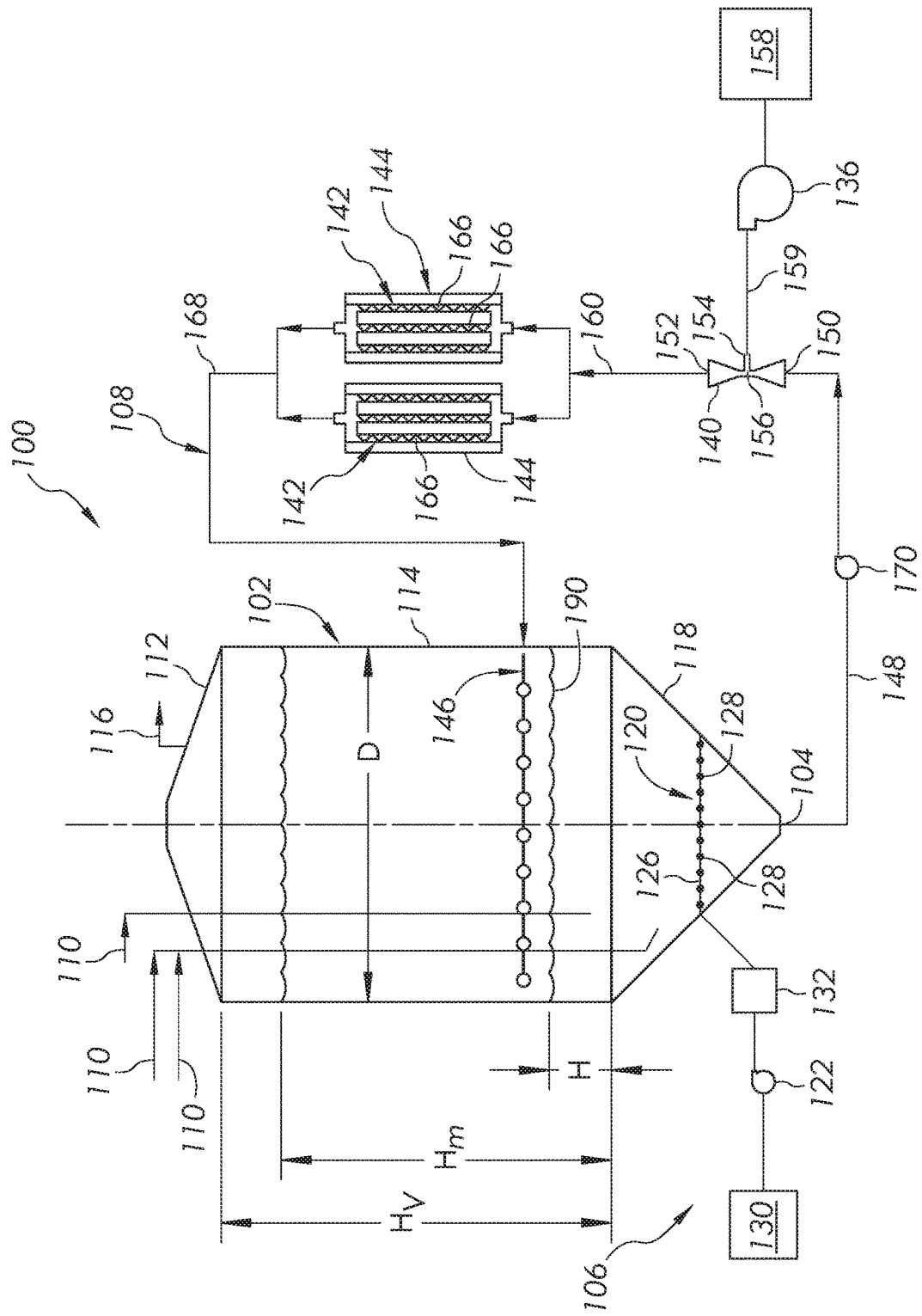
FIG. 1 schematically depicts a system for conducting aerobic fermentation, in accordance with one or more embodiments of the present disclosure.
Figure 4:
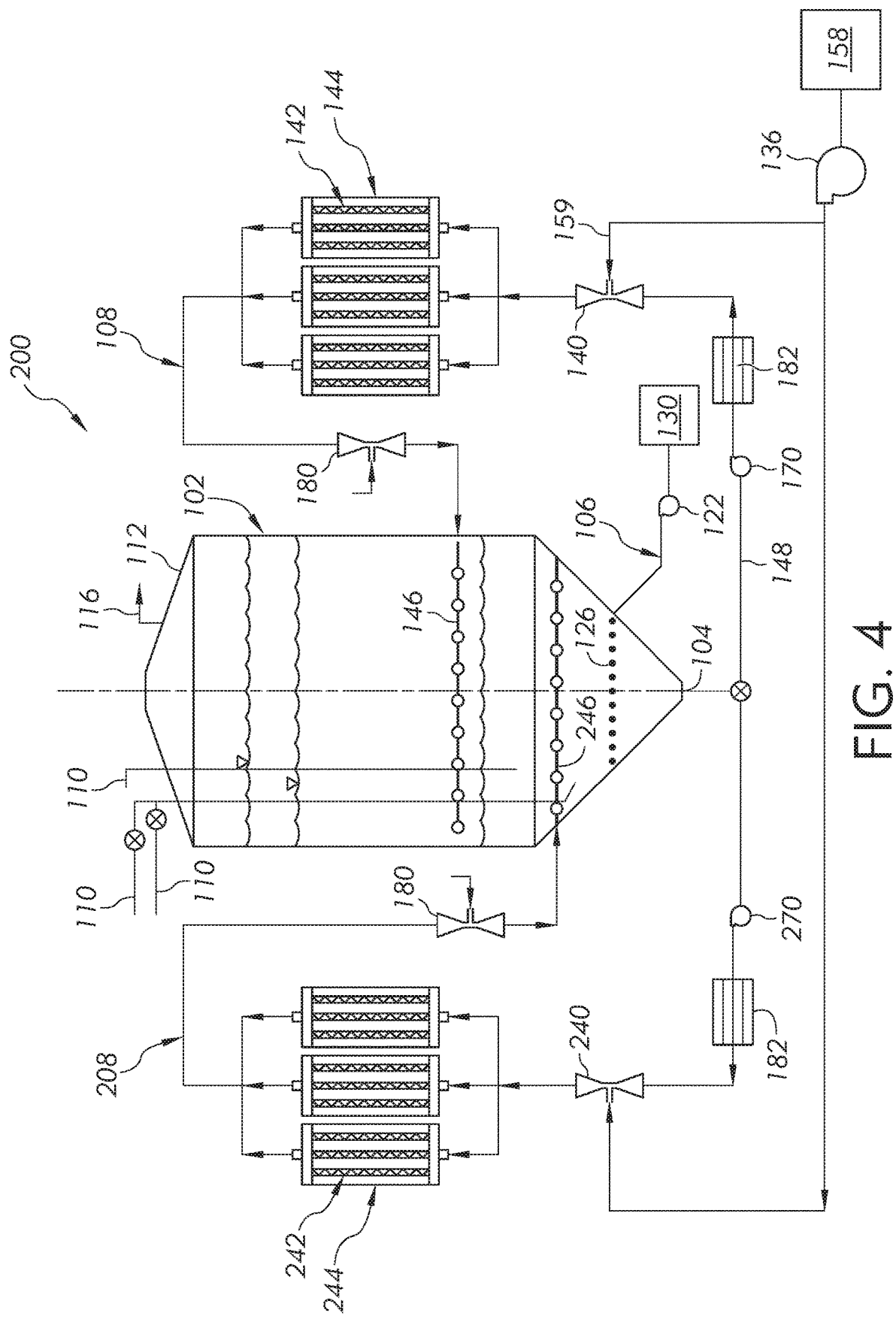
FIG. 4 schematically depicts another system for conducting aerobic fermentation, in accordance with one or more embodiments of the present disclosure.

For purposes of describing the simplified schematic illustrations and descriptions of FIGS. 1 and 4, the numerous valves, temperature sensors, electronic controllers and the like that may be employed and well known to those of ordinary skill in the art of certain chemical processing operations are not included. It should further be noted that arrows in the drawings refer to process streams. However, the arrows may equivalently refer to transfer lines which may serve to transfer process streams between two or more system components. Additionally, arrows that connect to system components define inlets or outlets in each given system component. The arrow direction corresponds generally with the major direction of movement of the materials of the stream contained within the physical transfer line signified by the arrow. Furthermore, arrows which do not connect two or more system components signify a product stream which exits the depicted system or a system inlet stream which enters the depicted system.

DETAILED DESCRIPTION

Embodiments of the present disclosure are directed to systems and methods for conducting aerobic fermentations. Specifically, the present embodiments are related to an aerobic fermentation system that comprises a vessel, an aeration system, and one or multiple recirculation loops fluidly coupled to the outlet of the vessel. The aeration system includes a gas sparger fluidly coupled to the vessel and positioned to introduce a compressed gas to an internal volume of the vessel. The recirculation loop comprises at least one eductor fluidly coupled to an oxygen-containing gas source, at least one static mixer downstream of the at least one eductor, at least one heat exchanger downstream of the at least one eductor, and at least one distributor downstream of the static mixer and the heat exchanger. The distributor is fluidly coupled to the internal volume of the vessel. When a fermentation composition is introduced to the vessel, the compressed gas from the gas sparger provides mixing to the fermentation composition, and a stream of the fermentation composition passes from the vessel into the recirculation loop, through the at least one educator, the at least one static mixer, and the at least one heat exchanger of the recirculation loop, and passes out of the at least one distributor back into the internal volume of the vessel. The aerobic fermentation system, including the aeration system and the recirculation loop, provides a sufficient oxygen mass transfer rate into the fermentation composition to maintain aerobic conditions for the aerobic fermentation conducted in large volume vessels and vessels having lesser aspect ratios compared to typical aerobic fermenters. For example, the aerobic fermentation system enables aerobic fermentation to be conducted in vessels having a volume of up to 4000 cubic meters ($m^3$) and an aspect ratio of up to 4.

As used in this disclosure, the "aspect ratio" of a vessel refers to the height of the fermentation composition in the vessel divided by the diameter of the vessel. The "maximum aspect ratio" of a vessel refers to the maximum height of the fermentation composition in the vessel divided by the diameter of the vessel.

As used in this disclosure, the "maximum height of the fermentation composition" in the vessel refers to the height of the fermentation composition in the vessel when the fermentation composition is at its largest possible safe volume in the vessel.

As used in this disclosure, the term "aerobic fermentation" refers to conversion of organic materials to one or a plurality of compounds through metabolism of the organic materials by microorganisms under aerobic conditions.

As used in this disclosure, the term "aerobic conditions" refers to conditions in the fermentation composition in which oxygen is present and available to the microorganisms in sufficient amounts to cause the microorganisms to favor processing the nutrients from the nutrient media using aerobic fermentation over processing the organic materials and nutrients through anaerobic fermentation.

As used in this disclosure, the term "fermentation composition" refers to a composition comprising at least microorganisms, such as bacteria, yeast, or other microbial species for example, and a nutrient medium that includes organic materials metabolized by the microorganisms. The fermentation composition may also include solvents, as water for example, and compounds produced during the aerobic fermentation process, such as gases, organic alcohols, organic acids, or other compounds. The fermentation composition may also include gases, such as oxygen-containing gases, introduced to the fermentation composition during the aerobic fermentation process. The composition of the fermentation composition may change throughout the course of a fermentation process as the nutrient medium is consumed and replenished, compounds are produced through microbial metabolism, and microorganism population changes.

As used in this disclosure, the "oxygen transfer rate" refers to the rate at which a certain mass of oxygen is transferred and dissolved into the liquid phase, such as the liquid phase of the fermentation composition.

Industrial chemicals and products, such as organic alcohols and acids for example, may be biologically synthesized through fermentation processes. In fermentation processes, organic materials are converted into one or more compounds by microorganisms. The microorganisms take in the organic materials, at least partially metabolize the organic materials into compounds, and discharge and/or accumulate the compounds, which may include organic alcohols, organic acids, or other organic compounds for example, that may be recovered from the fermentation broth as commercial products or industrial chemicals for use as raw materials and intermediates in further processing operations. Fermentations may be conducted under anaerobic conditions in which the concentration of dissolved oxygen in the fermentation composition is reduced (i.e., less than an amount sufficient to conduct aerobic fermentation) such that the microorganisms process the organic materials through anaerobic mechanisms. Alternatively, fermentations may be conducted under aerobic conditions in which the dissolved oxygen concentration in the fermentation composition is maintained at a level sufficient to provide the oxygen for the microorganisms to process the organic material through aerobic metabolism. Conducting fermentations under aerobic conditions instead of anaerobic conditions may modify the chemical composition of the compounds produced by the microorganisms.

Aerobic fermentation is highly exothermic. The heat generated by aerobic fermentation is removed from the fermentation composition to avoid overheating the system, which may cause death of the microorganisms. Additionally, aerobic fermentation proceeds under conditions in which the oxygen transfer rate into the fermentation composition is at least equal to or greater than the uptake rate of oxygen in the fermentation composition due to a given microbial metabolism.

Motorized and/or mechanical agitation of the fermentation composition throughout the aerobic fermentation process is used in some typical fermenters to achieve a level of gas-liquid contacting sufficient to provide sufficient oxygen mass transfer to the fermentation composition. However, as the volume of the fermentation composition in the fermenter increases, the size and power requirements for the motorized agitation to maintain sufficient oxygen mass transfer rates also increase. For example, a fermenter having a volume of greater than 1000 cubic meters ($m^3$) may require an agitation motor capacity of greater than 3000 hp. Motorized agitation systems of that capacity are capital intensive and generate substantial force within the vessel that may cause existing vessels to bow or burst under the heavy force load caused by the motorized agitation.

Furthermore, business needs may require changing from an anaerobic fermentation to an aerobic fermentation process. However, typical anaerobic fermenters may have substantially larger volumes compared to aerobic fermenters and may not be configured to achieve the mass transfer rates of oxygen to the fermentation composition that are necessary to maintain aerobic conditions in the fermentation composition. The systems for conducting aerobic fermentation disclosed herein may provide for efficient retrofitting of existing anaerobic fermenters to conduct aerobic fermentations.

Referring to FIG. 1, a system for conducting an aerobic fermentation is illustrated, the system generally identified by reference number 100. The system 100 includes a vessel 102 having at least one outlet 104, an aeration system 106 coupled to the vessel 102, and at least one recirculation loop 108 coupled to the outlet 104 of the vessel 102. The combination of the aeration system 106 and recirculation loop 108 may provide sufficient oxygen mass transfer into the fermentation composition to maintain aerobic conditions throughout the fermentation process. The vessel 102 may have a large volume compared to typical aerobic fermenters and the system 100 may provide sufficient oxygen mass transfer to maintain aerobic conditions without reliance on motorized agitation.

The vessel 102 generally includes a top 112, at least one sidewall 114, and a bottom 118. The vessel 102 has at least one outlet 104 and at least one inlet 110. The inlets 110 may be positioned in a top 112 of the vessel 102 or in a sidewall 114 proximal to the top 112 of the vessel 102. The inlets 110 provide a pathway for charging materials such as the fermentation composition (i.e., the microorganism culture, nutrient media, and/or solvent) to the vessel 102 and charging nutrient media to the fermentation composition throughout the fermentation process. The vessel 102 may include one or more vents 116 to vent gases from the vessel 102, such as excess gases from the aeration system 106 and/or gases generated by the microorganisms for example. The vessel 102 may have any convenient shape. In some embodiments, the vessel 102 may be a cylindrical vessel. In embodiments, the bottom 118 of the vessel 102 may be conical, dished, or otherwise sloped. The outlet 104 may be coupled to the bottom 118 of the vessel 102, such as at the lowest point of a conical or dished bottom of the vessel 102 for example.

The system 100 may enable the vessel 102 to have a lesser aspect ratio compared to typical aerobic fermenters. In embodiments, the vessel 102 may have a maximum aspect ratio of from 0.5 to 4, from 0.5 to 3, from 0.5 to 2, from 0.5 to 1, from 1 to 4, from 1 to 3, from 1 to 2, from 2 to 4, from 2 to 3, from or from 3 to 4, where the maximum aspect ratio of the vessel 102 is defined as the maximum height $H_m$ of the fermentation composition in the vessel 102 divided by an inside diameter D of the vessel 102. The maximum height $H_m$ of the fermentation composition in the vessel 102 may be equal to or less than a straight side height $H_v$ of the vessel 102. The vessel 102 may have an internal volume of from 100 $m^3$ to 4000 $m^3$, from 100 $m^3$ to 3000 $m^3$, from 100 $m^3$ to 2000 $m^3$, from 100 $m^3$ to 1000 $m^3$, from 300 $m^3$ to 4000 $m^3$, from 300 $m^3$ to 3000 $m^3$, from 300 $m^3$ to 2000 $m^3$, from 300 $m^3$ to 1000 $m^3$, from 500 $m^3$ to 4000 $m^3$, from 500 $m^3$ to 3000 $m^3$, from 500 $m^3$ to 2000 $m^3$, from 500 $m^3$ to 1000 $m^3$, from 1000 $m^3$ to 4000 $m^3$, from 1000 $m^3$ to 3000 $m^3$, from 1000 $m^3$ to 2000 $m^3$, or from 2000 $m^3$ to 4000 $m^3$. In some embodiments, the vessel 102 may be a recycled or repurposed anaerobic fermenter having the aeration system 106 and the recirculation loop 108 fluidly coupled thereto. In other embodiments, the vessel 102 may be a non-pressurized vessel, such as a converted ambient storage tank or other low pressure vessel for example.

The aeration system 106 comprises a sparger 120 and a compressor 122 for delivering a compressed gas, such as an oxygen-containing gas, to the sparger 120. The sparger 120 is fluidly coupled to the vessel 102 and positioned to introduce an oxygen-containing gas to the internal volume of the vessel 102. In some embodiments, the sparger 120 may include a sparging tube 126 having a plurality of openings 128 through which the oxygen-containing gas is introduced to the internal volume of the vessel 102. The sparger 120 is positioned in a bottom portion of the vessel 102 so that the oxygen-containing gas introduced by the sparger 120 flows up through the fermentation composition contained within the internal volume of the vessel 102. The sparging tube 126 may be shaped to introduce the oxygen-containing gas to the fermentation composition across at least a portion of the cross-section of the vessel 102. In some embodiments, the sparging tube 126 is shaped to introduce the oxygen-containing gas to the fermentation composition uniformly across the entire cross-section of the vessel 102. In some embodiments, the sparging tube 126 may include a main tube with a plurality of tubes extending horizontally outward from the main tube to deliver the oxygen-containing gas uniformly across the cross-section of the vessel 102. Alternatively, the sparging tube 126 may include a plurality of circular concentric tubes fluidly coupled together to deliver the oxygen-containing gas uniformly across the cross-section of the vessel 102. Other shapes of the sparging tube 126 are contemplated for delivering the oxygen-containing air uniformly across the cross-section of the vessel 102. In some embodiments, the sparging tube 126 of the sparger 120 may be formed integral with the vessel 102, such as by sintering or welding the sparging tube 126 to one or a plurality of ports in the bottom 118 or sidewall 114 of the vessel 102 or directly to the bottom 118 or the sidewall 114 of the vessel 102. In some embodiments, the sparging tube 126 may be removeably insertable into vessel 102 through one or more ports in the vessel 102.

The compressor 122 may be fluidly coupled to the sparger 120 to deliver the oxygen-containing gas to the sparger 120. The compressor 122 may also be fluidly coupled to an oxygen-containing gas source 130. The oxygen-containing gas may be a gas containing oxygen ($O_2$), such as ambient air, oxygen gas, oxygen-enriched air, or other oxygen-containing gas. The oxygen-containing gas source 130 may be a conduit open to ambient air, a volume of liquid or gaseous oxygen ($O_2$) such as an oxygen tank, an oxygen-enriched gas stream produced using an oxygen production process, an oxygen-containing gas stream from other chemical process operations, other sources of oxygen-containing gas, or combinations of these. The aeration system 106 may also optionally include an air sterilizing system 132 for removing contaminants from the oxygen-containing gas prior to introducing the oxygen-containing gas to the vessel 102. The air sterilizing system 132 may be positioned downstream of the compressor 122 such that the oxygen-containing gas passes from the compressor 122, through the air sterilizing system 132, and to the sparger 120. Contaminants in the oxygen-containing gas may decrease yield from the fermentation process by poisoning the microorganisms in the fermentation composition or changing the metabolism pathway of the microorganisms. Alternatively, if the contaminants are other microorganisms, these may outcompete the original microorganisms for the consumption of organic materials and produce a different set of compounds and/or products. The air sterilization system may include an air filter, ozone sterilization system, ultraviolet (UV) sterilization system, or combinations of these sterilizations systems. In some embodiments, the air sterilizing system 132 may be a filter, such as a 1 micron filter for example.

In operation of the aeration system 106, the compressor 122 draws the oxygen-containing gas from the oxygen-containing gas source 130 and compresses the oxygen-containing gas. The oxygen-containing gas is then passed through the optional air sterilizing system 132, where one or more contaminants, such as particulates or entrained liquids for example, are removed from the oxygen-containing gas. The oxygen-containing gas is then passed to the sparger 120. The oxygen-containing gas flows through the sparging tube 126 and exits the sparging tube 126 from the plurality of openings 128 in the sparging tube 126 into the internal volume of the vessel 102. Bubbles of the oxygen-containing gas exiting the openings 128 of the sparging tube 126 move upward through the fermentation composition in the vessel 102. The sparger 120 may generate churning turbulent flow throughout the vessel 102 and prevent macro-flows from developing within the vessel 102. Generating churning turbulent flow through the vessel 102 and preventing development of macro-flows may improve the oxygen transfer rate into the fermentation composition. The compressor 122 may deliver the oxygen-containing gas to the sparger 120 at a pressure sufficient to cause the sparger 120 to generate the churning turbulent flow throughout the vessel 102. As the oxygen-containing gas exits the sparger 120 and migrates upward through the fermentation composition in the vessel 102, oxygen from the oxygen-containing gas transfers from the gas phase of the bubbles to the liquid phase of the fermentation composition, thereby at least partially oxygenating the fermentation composition.

The oxygen mass transfer rate from the gas phase to the liquid fermentation composition by way of the sparger 120 may be influenced by the bubble size of the oxygen-containing gas introduced to the vessel 102, the flow rate of the oxygen-containing gas into the vessel 102, the height H of the liquid in the vessel 102, the viscosity of the fermentation composition, the concentration of oxygen in the oxygen-containing gas, and the pressure within the vessel 102. For example, decreasing the bubble size increases the surface area for mass transfer and, therefore, increases the mass transfer rate of oxygen into the fermentation composition. Bubble size may be modified by changing the size of the openings 128 in the sparging tube 126. Alternatively, fine bubble diffusers may be installed on one or more than one of the openings 128 in the sparging tube 126 to diffuse the oxygen-containing gas into a plurality of smaller bubbles. Additionally, the mass transfer rate of oxygen into the fermentation composition may be modified by changing the flow rate of the oxygen-containing gas delivered into the fermentation composition. Increasing the flow rate of the oxygen-containing gas may increase the number of bubbles introduced to the fermentation composition, which also increases the surface area of mass transfer. The flow rate of the oxygen-containing gas may be controlled by controlling the pressure of the oxygen containing gas generated by the compressor 122.

The mass transfer rate of oxygen into the fermentation composition may be further controlled by controlling the concentration of oxygen in the oxygen-containing gas. Increasing the oxygen concentration in the oxygen-containing gas, such as by enriching ambient air with oxygen for example, creates a greater concentration gradient between the oxygen-containing gas and the fermentation composition. The greater concentration gradient between the oxygen-containing gas and the fermentation composition increases mass transfer rate of the oxygen into the fermentation composition.

The height H of the fermentation composition in the vessel 102 and the viscosity of the fermentation composition in the vessel 102 both influence the residence time of the oxygen-containing gas in the fermentation composition. For example, as the height H of the fermentation composition in the vessel 102 increases, the residence time between the bubbles of oxygen-containing gas and the fermentation composition increases and the effectiveness of oxygen mass transfer from the gas phase to the fermentation composition also increases. Increasing viscosity of the fermentation composition also increases the residence time of the oxygen-containing gas bubbles with the fermentation composition, which also increases the mass transfer rate of oxygen into the fermentation composition.

In a typical aerobic fermenter, the pressure in the aerobic fermenter may also influence the mass transfer rate of oxygen to the fermentation composition. Typical aerobic fermenters operate at positive pressure, and increasing the pressure in the fermenter may increase the mass transfer rate of oxygen to the fermentation composition. The system 100 disclosed herein having the aeration system 106 and the recirculation system 108 provides a sufficient mass transfer rate of oxygen to the fermentation composition without having to conduct the aerobic fermentation under positive pressure conditions. Thus, the aerobic fermentation process may be conducted in system 100 at ambient pressure. By providing sufficient mass transfer rates of oxygen without conducting the aerobic fermentation under pressure, the system 100 may enable the use of non-pressurized tanks as the vessel 102. Non-pressurized tanks may have thinner walls and substantially lower cost than pressure vessels.

Referring again to FIG. 1, the recirculation loop 108 is fluidly coupled to the outlet 104 of the vessel 102. The recirculation loop 108 is positioned external to the vessel 102 and includes an eductor 140, at least one static mixer 142 downstream of the eductor 140, at least one heat exchanger 144 downstream of the eductor 140, and a distributor 146. In embodiments, the eductor 140 is a Venturi device having an eductor liquid inlet 150, an eductor outlet 152, and an eductor gas inlet 154. The eductor gas inlet 154 is fluidly coupled to a narrowed section 156 of the Venturi device. The gas inlet 154 is also fluidly coupled to an oxygen-containing gas source 158. The oxygen-containing gas 159 may be ambient air, oxygen gas, oxygen-enriched air, or other oxygen-containing gas. The oxygen-containing gas source 158 may be a port fluidly coupled to ambient air, a contained volume of liquid or gaseous oxygen such as an oxygen tank, an oxygen-enriched gas stream produced using an oxygen production process, an oxygen-containing gas stream from other chemical process operations, other sources of oxygen-containing gas, or combinations of these. In some embodiments, the oxygen-containing gas source 158 may be the same as the oxygen-containing gas source 130 fluidly coupled to the aeration system 106. Alternatively, in other embodiments, the oxygen-containing gas source 158 for the recirculation loop 108 may be separate from the oxygen-containing gas source 130 fluidly coupled to the aeration system 106.

A compressor 136 may be fluidly coupled to the oxygen-containing gas source 158 and the eductor gas inlet 154. The compressor 136 may deliver the oxygen-containing gas from the oxygen-containing gas source 158 to the eductor gas inlet 154. The oxygen-containing gas source 158 may also optionally include an air sterilizing system (not shown) for removing contaminants from the oxygen-containing gas 159 prior to introducing the oxygen-containing gas 159 to the eductor 140.

The fermentation composition stream 148 is a multiphase stream having a liquid phase and a solid phase or a liquid phase, a solid phase, and a gas phase. The gas phase of the fermentation composition stream 148 may include bubbles of the oxygen-containing gas introduced by the aeration system 106, bubbles of gas generated from microbial metabolism, or both, for example. The liquid phase may include at least one of the nutrient media, solvent, liquid compounds produced by the microorganisms during the aerobic fermentation, other liquid components, or combinations of these. The solid phase may include at least the microorganisms and may include solid compounds produced by the microorganisms, other solid components of the fermentation composition, or combinations of these.

The fermentation composition stream 148 passes from the eductor liquid inlet 150, through the narrowed section 156 of the eductor 140, and out of the eductor outlet 152. The oxygen-containing gas is introduced to the narrowed section 156 of the eductor 140 through eductor gas inlet 154. The oxygen-containing gas at least partially mixes with the fermentation composition as the fermentation composition passes through the narrowed section 156 of the eductor 140. The stream exiting the eductor 140 from the eductor outlet 152 is a combined stream 160 that includes the fermentation composition stream 148 and the oxygen-containing gas 159. The combined stream 160 is a multiple-phase mixture that includes a liquid phase, a solid phase, and a gas phase. The gas phase may include the oxygen-containing gas 159 introduced by the eductor 140 as well as gases entrained in the fermentation composition stream 148 entering the eductor 140, such as gas compounds from microbial metabolism, entrained gas bubbles from the aeration system, or both, for example.

The size of the eductor 140 may be defined by the nominal diameter of the fittings at the eductor liquid inlet 150 and the eductor outlet 152. The eductor 140 may have a size of from 0.025 meter (m) to 1 m, from 0.025 m to 0.5 m, from 0.025 m to 0.1 m, from 0.025 m to 0.05 m, from 0.05 m to 1 m, from 0.05 m to 0.5 m, from 0.05 m to 0.1 m, from 0.1 m to 1 m, from 0.1 m to 0.5 m, or from 0.5 m to 1 m. A shape of the eductor 140, such as the shape of the narrowed section 156 and the cross-sectional size of the eductor gas inlet 154 for example, may influence the amount of oxygen-containing gas 159 introduced to the fermentation composition stream 148 passing through the eductor 140. In embodiments, the eductor 140 may be shaped to provide a volume flow ratio of the oxygen-containing gas 159 to the fermentation composition stream 148 sufficient to oxygenate the fermentation composition (i.e., here referring generally to the fermentation composition through the fermentation process, such as the fermentation composition in the vessel 102 as well as the fermentation composition recirculated through the recirculation loop 108). In some embodiments, the eductor 140 may provide a volume flow ratio of the oxygen-containing gas 159 to the fermentation composition stream 148 (i.e., ratio of the gas volumetric flow rate to the liquid volumetric flow rate) of from 0.05 to 1, from 0.05 to 0.8, from 0.05 to 0.6, from 0.05 to 0.4, from 0.05 to 0.2, from 0.05 to 0.1, from 0.05 to 07, from 0.07 to 1, from 0.07 to 0.8, from 0.07 to 0.6, from 0.07 to 0.4, from 0.07 to 0.2, from 0.07 to 0.1, from 0.1 to 1, from 0.1 to 0.8, from 0.1 to 0.6, from 0.1 to 0.4, from 0.2 to 1, from 0.2 to 0.8, from 0.2 to 0.6, from 0.2 to 0.4, from 0.4 to 1, from 0.4 to 0.8, from 0.4 to 0.6, from 0.6 to 1, from 0.6 to 0.8, or from 0.8 to 1.

In some embodiments, the recirculation loop 108 may include a fine bubble generator (not shown) in place of or in addition to the eductor 140 for introducing the oxygen-containing gas 159 to the fermentation composition stream 148. Other systems are contemplated for introducing the oxygen-containing gas to the fermentation composition in the recirculation loop 108 of the system 100.

Reducing the length of the recirculation loop 108 may reduce bio-fouling of surface areas of components of the recirculation loop 108. However, reducing the length of the recirculation loop 108 results in a decrease in the residence time of the fermentation composition in the recirculation loop 108. High oxygen transfer rates in the recirculation loop 108 may provide oxygen saturation of the fermentation composition in these reduced residence times. The recirculation loop 108 may provide high oxygen transfer rates by introducing the combined stream 160 comprising the fermentation composition and oxygen-containing gas to one or a plurality of static mixers 142 to reduce the size of the bubbles of oxygen-containing gas in the combined stream 160.

Figure 2:
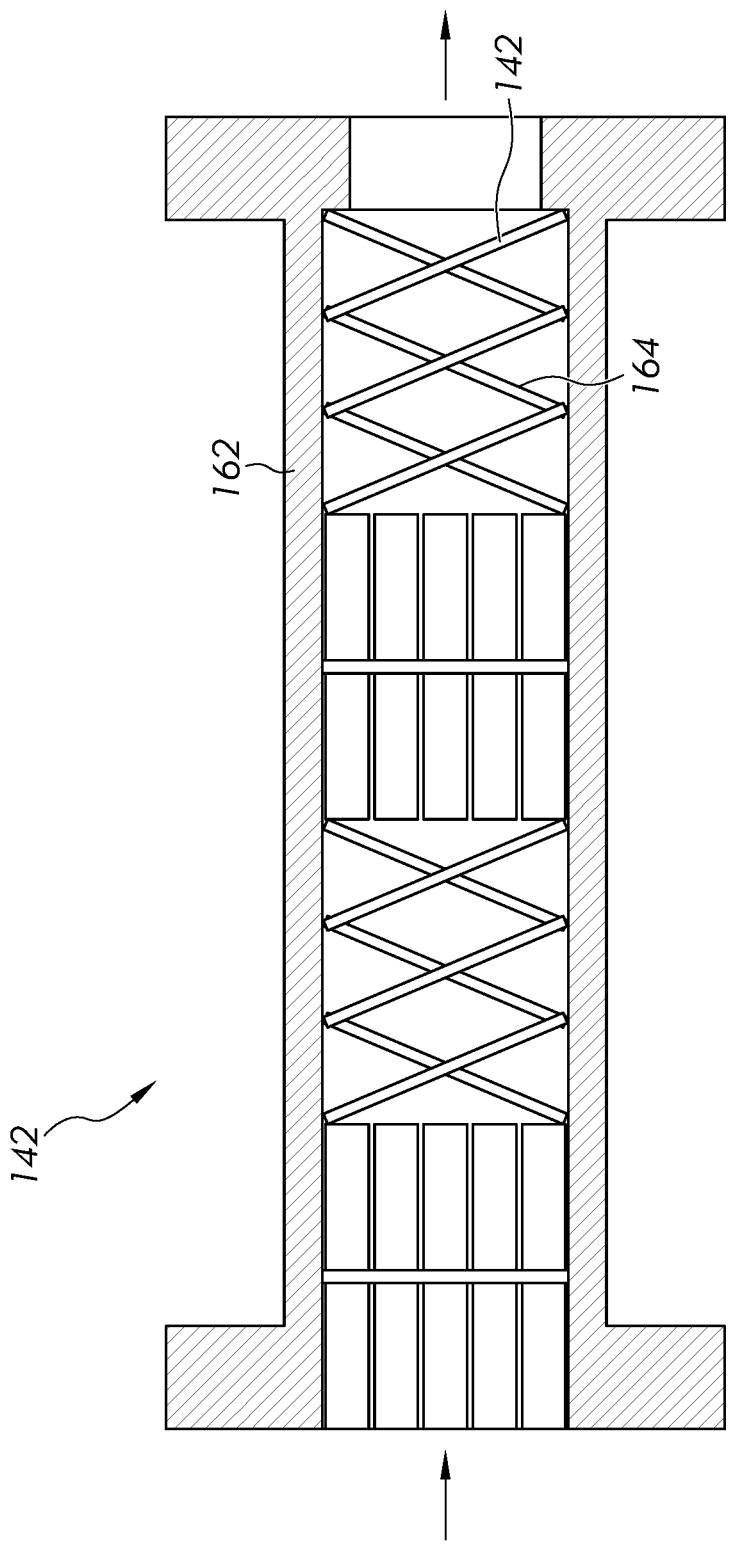
FIG. 2 schematically depicts a static mixer of the system for conducting aerobic fermentation of FIG. 1, in accordance with one or more embodiments of the present disclosure.

The static mixers 142 are positioned in the recirculation loop 108 downstream of the eductor 140. The eductor outlet 152 is fluidly coupled to the static mixer 142. Referring to FIG. 2, the static mixer 142 is disposed within a conduit 162, such as a conduit of heat exchanger 144 for example. In embodiments, the static mixer 142 may include a plurality of baffles 164 shaped and positioned to intensify flow turbulence to the combined stream 160 flowing through the static mixer 142. In some embodiments, the baffles 164 may include a plurality of crisscrossing baffles. Alternatively, in other some embodiments, the baffles 164 may be helical baffles. Other shapes and orientations are contemplated for the baffles 164 of the static mixer 142. The static mixer 142 breaks the gas phase of the combined stream 160 into smaller-sized bubbles by introducing flow turbulence to the combined stream 160. Reducing the bubble size of the gas phase in the combined stream 160 increases the total surface area of the interface between the liquid phase and the gas phase. The oxygen mass transfer rate from the gas phase to the liquid phase is proportional to the surface area of the interface between the liquid phase and gas phase. Therefore, increasing the surface area by decreasing the bubble size of the gas phase increases the oxygen mass transfer rate from the oxygen-containing gas into the liquid phase of the fermentation composition.

In embodiments, the static mixer 142 may produce turbulent fluid flow conditions that, when combined with the aeration system 106, are capable of maintaining an oxygen mass transfer rate equal to or greater than the oxygen uptake rate due to microbial metabolism during the initial stages of the aerobic fermentation process, when the volume of fermentation composition in the vessel 102 is low. In some embodiments, the static mixer 142 may produce fluid flow conditions sufficient to reduce the bubble size of the oxygen-containing gas phase to increase the oxygen mass transfer into the fermentation composition. In some embodiments, the static mixer 142 may produce fluid flow having a Reynolds number of from 2000 to 10,000, from 2000 to 8000, from 2000 to 6000, from 2000 to 4000, from 4000 to 10,000, from 4000 to 8000, from 4000 to 6000, from 6000 to 10,000, from 6000 to 8000, or from 8000 to 10,000. The Reynolds number for flow through the recirculation loop is defined as $$Re = \frac{\rho_l U_l D_{pipe}}{\mu_l} \quad \text{Equation 1}$$

where $\rho_l$ and $\mu_l$ are the liquid density and dynamic viscosity, respectively, $D_{pipe}$ is the diameter of the pipe which is equipped with the static mixers, and $U_l$ is the velocity of the fermentation composition through the pipe.

In embodiments, an average liquid velocity of the combined stream 160 in the static mixer 142 may be sufficient to generate the fluid flow conditions in the static mixer 142 that, when combined with the aeration system 106, are sufficient to maintain an oxygen mass transfer rate equal to or greater than the oxygen uptake rate due to microbial metabolism during the initial stages of the aerobic fermentation process, when the volume of fermentation composition in the vessel 102 is low. The initial stages of the aerobic fermentation process may include the first third of the aerobic fermentation process during which time the volume of fermentation composition in the vessel 102 is low. In embodiments, the average liquid velocity of the combined stream 160 in the static mixer 142 may be from 0.2 meters per second (m/s) to 2 m/s, from 0.2 m/s to 1.6 m/s, from 0.2 m/s to 1.2 m/s, from 0.2 m/s to 0.8 m/s, from 0.2 m/s to 0.4 m/s, from 0.4 m/s to 2 m/s, from 0.4 m/s to 1.6 m/s, from 0.4 m/s to 1.2 m/s, from 0.4 m/s to 0.8 m/s, from 0.8 m/s to 2 m/s, from 0.8 m/s to 1.6 m/s, from 0.8 m/s to 1.2 m/s, from 1.2 m/s to 2 m/s, from 1.2 m/s to 1.6 m/s, or from 1.6 m/s to 2 m/s.

Referring back to FIG. 1, in some embodiments, the recirculation loop 108 may include a plurality of static mixers 142 positioned downstream of the eductor 140. A portion of the static mixers 142 may be disposed in parallel with one another. The static mixers 142, as well as other equipment in the recirculation loop 108, may be susceptible to biofouling during continuous operation of the system 100. Biofouling refers to the buildup of cells and other materials on the internal surfaces of the static mixers 142, heat exchangers 144, eductor 140, pump 170, and the other equipment. Arranging the static mixers 142 in parallel enables one or more of the static mixers 142 to be taken off-line for cleaning and sterilization without shutting down the system 100. Alternatively, one or more static mixers 142 may by positioned in series to increase the mixing of the combined stream 160.

As shown in FIG. 1, the heat exchangers 144 are positioned downstream of the eductor 140. The heat exchangers 144 may include a shell-and-tube heat exchanger, a plate-and-frame heat exchanger, or both. Other types of heat exchangers may be suitable for the recirculation loop 108. As previously described, heat is generated by microbial metabolism during fermentation and is retained in the fermentation composition stream 148 introduced to the recirculation loop 108 and the combined stream 160 exiting the eductor 140. The heat exchangers 144 transfer at least a portion of this heat from the combined stream 160 to a heat sink, such as a heat transfer fluid for example. Removal of heat from the combined stream 160 by the heat exchangers 144 reduces the temperature of the combined stream 160. Removal of heat using the heat exchangers 144 maintains the temperature of the fermentation composition in the vessel 102 and may prevent overheating, which may lead to death of the microorganisms.

In some embodiments, the heat exchangers 144 may have a heat transfer capacity sufficient to remove enough heat from the combined stream 160 to maintain a constant temperature of the fermentation composition in the vessel 102 at a maximum volume of fermentation composition in the vessel 102. In embodiments, each of the heat exchangers 144 may have a heat transfer capacity of 50 kilowatts (kW) to 1,000 kW, from 50 kW to 800 kW, from 50 kW to 600 kW, from 50 kW to 400 kW, from 50 kW to 200 kW, from 50 kW to 100 kW, from 100 kW to 1,000 kW, from 100 kW to 800 kW, from 100 kW to 600 kW, from 100 kW to 400 kW, from 100 kW to 200 kW, from 200 kW to 1,000 kW, from 200 kW to 800 kW, from 200 kW to 600 kw, from 200 kW to 400 kW, from 400 kW to 1,000 kW, from 400 kW to 800 kw, from 400 kW to 600 kW, from 600 kW to 1,000 kW, from 600 kW to 800 kW, or from 800 kW to 1,000 kW.

In some embodiments, the recirculation loop 108 may include a plurality of heat exchangers 144 positioned downstream of the eductor 140. At least some of the heat exchangers 144 may be disposed in parallel with one another. Like the static mixers 142, the heat exchangers 144 may be susceptible to biofouling during continuous operation of the system 100. Arranging the heat exchangers 144 in parallel enables one or more of the heat exchangers 144 to be isolated from the recirculation loop 108 and taken off-line for cleaning and sterilization without shutting down the system 100 and disrupting the fermentation process. Alternatively, one or more heat exchangers 144 may be positioned in series to increase the transfer of heat out of the combined stream 160. In embodiments, the recirculation loop 108 may have a number of heat exchangers 144 that is sufficient to remove the heat generated by microbial metabolism during the fermentation process and maintain a constant temperature of the fermentation composition in the system 100. In some embodiments, the recirculation loop 108 may have 1, 2, 3, 4, 5, 6, 7, 8, 9, 10, 11, or 12 heat exchangers 144.

As shown in FIG. 1, in some embodiments, the static mixers 142 may be combined with the heat exchangers 144. In embodiments, each of the heat exchangers 144 may include a plurality of flow conduits 166 extending through the heat exchanger 144. The static mixers 142 may be disposed within each of the flow conduits 166 of the heat exchangers 144. The heat exchangers 144 having the static mixers 142 incorporated therein may be fluidly coupled to the eductor outlet 152. In operation, the combined stream 160 comprising the fermentation fluid and the oxygen-containing gas passes from the eductor outlet 152 into the heat exchangers 144. In the heat exchangers 144, the combined stream 160 passes through the static mixers 142. The combined stream 160 is mixed by the static mixers 142, and the mixing improves oxygen mass transfer from the gas phase to the liquid phase of the combined stream 160. Heat is simultaneously removed from the combined stream 160 by the heat exchanger 144. Providing static mixing of the combined stream 160 in the heat exchanger 144 may also improve the heat transfer rate of heat out of the combined stream 160. Additionally, incorporating the static mixers 142 into the heat exchangers 144 may also reduce the length of the recirculation loop 108. Reducing the length of the recirculation loop 108 may reduce the rate of biofouling of internal surfaces of the eductor 140, static mixers 142, heat exchangers 144, pump 170, piping, and other equipment of the recirculation loop 108.

As previously discussed, with a plurality of heat exchangers 144 operated in parallel in the recirculation loop 108, each heat exchanger 144 may be easily isolated from the recirculation loop 108 and sterilized independent of other equipment of the system 100 during operation of the system 100 and fermentation process. As a result, incorporation of the static mixers 142 into the heat exchangers 144 may provide for improved ability to sterilize the static mixers 142 during operation of the fermentation process, thereby mitigating fouling of the static mixers 142. Additionally, incorporating the static mixers 142 into the heat exchangers 144 may reduce the space footprint of the system 100, reduce the number of components to individually and independently sterilize during operation of the system 100, and provide for improved heat transfer from the combined stream 160 compared to a recirculation loop 108 in which the static mixers 142 are not integrated with the heat exchangers 144 but are positioned upstream or downstream of the heat exchangers 144.

Static mixing of and heat removal from the combined stream 160 produces an oxygenated fermentation composition 168 at the outlet of the heat exchanger 144. The oxygenated fermentation composition 168 includes an increased amount of dissolved oxygen in the liquid phase compared to the fermentation composition stream 148 introduced to the recirculation loop 108 at the outlet 104 of the vessel 102. The oxygenated fermentation composition 168 may also include an oxygen-depleted gas phase having an amount of oxygen less than the oxygen-containing gas introduced to the eductor 140.

Referring to FIG. 1, the oxygenated fermentation composition 168 exits the heat exchangers 144 and passes through the distributor 146 back into the vessel 102. The distributor 146 may be shaped to re-introduce the oxygenated fermentation composition 168 to the vessel 102 over at least a portion of the cross-section of the vessel 102. In some embodiments, the distributor 146 is shaped to distribute the oxygenated fermentation composition 168 to the vessel 102 uniformly over the entire cross-section of the vessel 102. In some embodiments, the distributor 146 may include a main tube with a plurality of tubes extending horizontally outward from the main tube to deliver the oxygenated fermentation composition 168 uniformly over the cross-section of the vessel 102. Alternatively, the distributor 146 may include a plurality of circular concentric tubes fluidly coupled together to deliver the oxygenated fermentation composition 168 uniformly over the entire cross-section of the vessel 102. Other shapes of the distributor 146 are contemplated for delivering the oxygenated fermentation composition 168 uniformly over the cross-section of the vessel 102.

Figure 3:
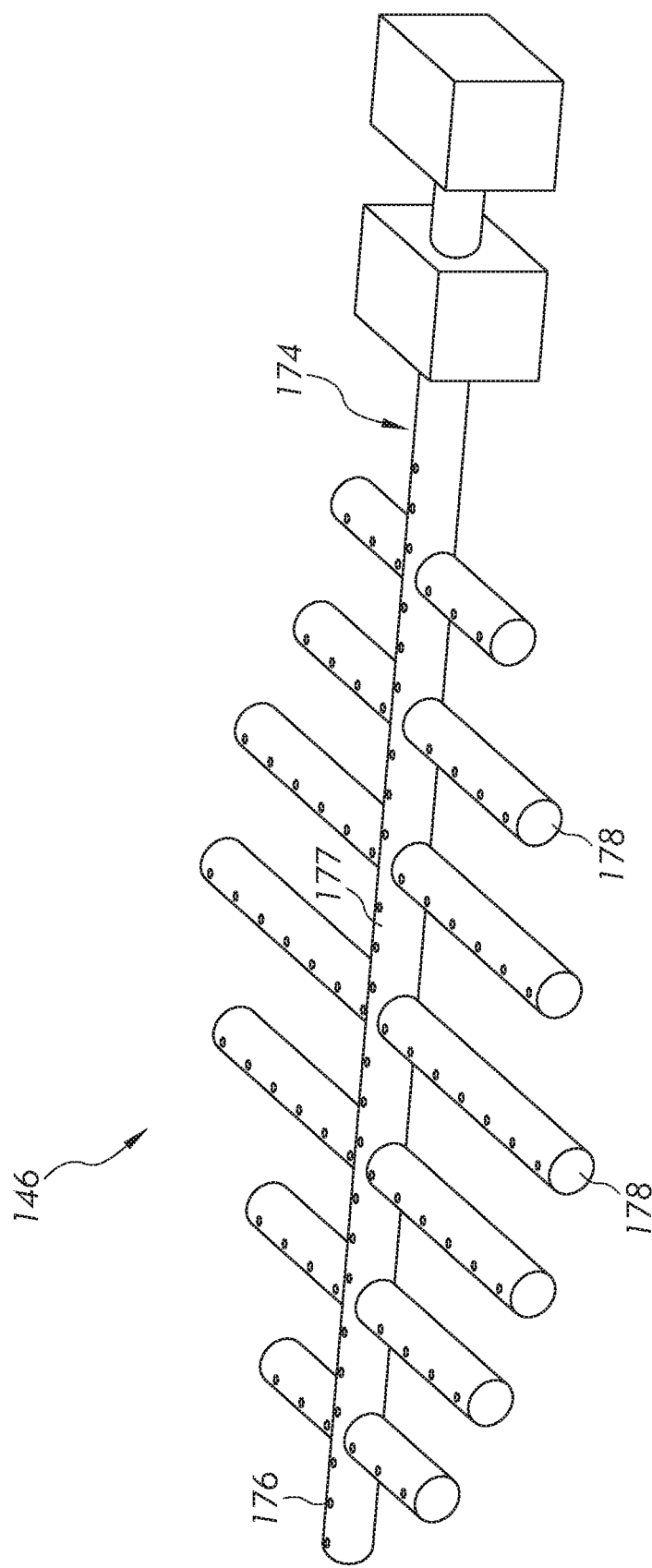
FIG. 3 schematically depicts a distributor of the system for conducting aerobic fermentation of FIG. 1, in accordance with one or more embodiments of the present disclosure.

Referring to FIG. 3, a non-limiting embodiment of the distributor 146 is illustrated as including at least a tube 174 having a plurality of holes 176 fluidly coupled to the internal volume of the vessel 102. The tube 174 of the distributor 146 may include a central tube 177 and a plurality of branches 178 extending outward from the central tube 177. The central tube 177 and each of the branches 178 include the plurality of holes 176 for distributing the oxygenated fermentation composition 168 back into the vessel 102. The branches 178 may extend outward from the central tube 177 so that the oxygenated fermentation composition 168 is distributed uniformly over the entire cross-section the vessel 102.

Referring back to FIG. 1, the distributor 146 may enter the internal volume of the vessel 102 through a port disposed in the sidewall 114 of the vessel 102 as shown in FIG. 1. Alternatively, the distributor 146 may pass through the top 112 of the vessel 102 and extend down into the internal volume of the vessel 102. In some embodiments, the distributor 146 may be positioned so that the tubes 174 of the distributor 146 are submerged in the fermentation composition disposed in the vessel 102 throughout the fermentation process.

In operation of the distributor 146, the oxygenated fermentation composition 168 passes from the recirculation loop 108 into the tube 174 of the distributor 146. The oxygenated fermentation composition 168 passes through the tube 174, including the central tube 177 and branches, and exits the distributor 146 through the holes 176 in tube 174 and into the vessel 102, where the oxygenated fermentation composition 168 mixes with the fermentation composition in the vessel 102.

Referring to FIG. 1, the recirculation loop 108 includes a pump 170 for moving the fermentation composition stream 148 through the recirculation loop 108. The pump 170 may be a multiphase pump capable of pumping the fermentation composition stream 148. As previously discussed, the fermentation composition stream 148 may be a multiphase stream having a liquid phase and a solid phase, a liquid phase and a gas phase, or a liquid phase, solid phase and a gas phase. In embodiments, the pump 170 may be positioned upstream of the eductor 140. The pump 170 may provide a liquid flow rate through the recirculation loop 108 of from 0.04 cubic meters per minute (m$^3$/min) to 20 m$^3$/min, from 0.04 m$^3$/min to 15 m$^3$/min, from 0.04 m$^3$/min to 10 m$^3$/min, from 0.04 m$^3$/min to 5 m$^3$/min, from 0.1 m$^3$/min to 20 m$^3$/min, from 0.1 m$^3$/min to 15 m$^3$/min, from 0.1 m$^3$/min to 10 m$^3$/min, from 0.1 m$^3$/min to 5 m$^3$/min, from 1 m$^3$/min to 20 m$^3$/min, from 5 m$^3$/min to 15 m$^3$/min, from 5 m$^3$/min to 10 m$^3$/min, from 5 m$^3$/min to 20 m$^3$/min, from 5 m$^3$/min to 15 m$^3$/min, from 5 m$^3$/min to 10 m$^3$/min, or from 10 m$^3$/min to 20 m$^3$/min.

The recirculation loop 108 may optionally include a secondary eductor 180 (FIG. 4) positioned downstream of the heat exchangers 144 and static mixers 142 of the recirculation loop 108. The secondary eductor 180 may be positioned upstream of the distributor 146. The secondary eductor 180 may be fluidly coupled to the oxygen-containing gas source 158 supplying eductor 140 or another oxygen-containing gas source. The secondary eductor 180 may introduce additional oxygen-containing gas to the oxygenated fermentation composition 168 as the oxygenated fermentation composition 168 passes through the secondary eductor 180. The oxygenated fermentation composition 168 having the additional oxygen-containing gas entrained therein passes to the distributor 146 and back into the vessel 102.

The recirculation loop 108 may also optionally include at least one secondary heat exchanger 182 (FIG. 4). In embodiments, the secondary heat exchanger 182 may be positioned upstream of the eductor 140. The secondary heat exchanger 182 may include a shell-and-tube heat exchanger, a plate-and-frame heat exchanger, or both. Other types of heat exchangers may be suitable for the secondary heat exchanger 182. The secondary heat exchanger 182 may provide additional heat removal from the fermentation composition stream 148.

Referring to FIG. 4, another system 200 for conducting aerobic fermentations may include the vessel 102, aeration system 106, the recirculation loop 108, and one or a plurality of supplemental recirculation loops 208. Each supplemental recirculation loop 208 may include a supplemental eductor 240, supplemental static mixers 242, supplemental heat exchangers 244, and a supplemental distributor 246. The supplemental recirculation loop 208 may also include a supplemental pump 270. The supplemental recirculation loop 208, supplemental eductor 240, supplemental static mixers 242, supplemental heat exchangers 244, supplemental distributor 246, and supplemental pump 270 may have any of the properties and characteristics described above in relation to the recirculation loop 108, eductor 140, static mixers 142, heat exchangers 144, distributor 146, and pump 170, respectively.

While conducting an aerobic fermentation in the system 200, the system 200 may circulate the fermentation composition through the recirculation loop 108, the supplemental recirculation loop 208, or both the recirculation loop 108 and the supplemental recirculation loop 208. In some embodiments, one of the recirculation loop 108 or the supplemental recirculation loop 208 may be taken off-line periodically to sterilize components, such as the heat exchangers 144, supplemental heat exchangers 244, static mixers 142, or supplemental static mixers 242 for example, during operation of the system 200. In some embodiments, the system 200 may be configured to alternate between circulating the fermentation composition through the recirculation loop 108 and circulating the fermentation composition through the supplemental recirculation loop 208. In embodiments having multiple supplemental recirculation loops 208, the system 200 may circulate the fermentation composition through all or less than all of the supplemental recirculation loops 208 and recirculation loop 108.

Referring back to FIG. 1, in operation of the system 100 for conducting aerobic fermentation, the fermentation composition comprising at least the microorganisms for conducting the fermentation and an amount of nutrient media is introduced to the vessel 102 up to a starting level 190. The aeration system 106 passes oxygen-containing gas into the fermentation composition in the vessel 102. In particular, the oxygen-containing gas from the oxygen-containing gas source 130 is compressed by the compressor 122 and passed through the sparger 120 into the fermentation composition in the vessel 102. As bubbles of the oxygen-containing gas from the aeration system 106 travel upward through the fermentation composition, oxygen from the oxygen containing gas transfers across the phase boundary into the fermentation composition to oxygenate the fermentation composition. At least a portion of the heat generated by microbial metabolism may be removed by the aeration system 106.

Simultaneously, the fermentation composition is drawn from the outlet 104 of the vessel 102 and passed into the recirculation loop 108 as fermentation composition stream 148. The fermentation composition stream 148 passes through the eductor 140 where oxygen-containing gas from the oxygen-containing gas source 158 is introduced to the fermentation composition stream 148 by the Venturi effect to produce a combined stream 160. The combined stream 160 is a multiphase stream that includes the fermentation composition in a liquid phase or a combination of solid and liquid phases and the oxygen-containing gas in the gas phase. The combined stream 160 passes to the static mixers 142. The static mixers 142 introduce flow turbulence into the combined stream 160 to increase the oxygen mass transfer rate from the gas phase into the liquid phase to produce an oxygenated fermentation composition 168. The oxygenated fermentation composition 168 may pass through the heat exchangers 144 to remove heat from the oxygenated fermentation composition 168. In some embodiments, the static mixers 142 may be integral with the heat exchangers 144, and the combined stream 160 may simultaneously pass through the static mixers 142 and heat exchangers 144 to introduce flow turbulence to facilitate oxygen mass transfer and remove heat at the same time. Upon passing out of the heat exchangers 144, the oxygenated fermentation composition 168 passes through the distributor 146 and back into the vessel 102. The recirculation loop 108 provides additional mixing of the fermentation composition in the vessel 102. Operation of the recirculation loop 108 may eliminate dead zones in the vessel 102. Dead zones refer to volumes of the fermentation composition in the vessel 102 that are impacted by sparger 120 and remain stationary without being mixed with the rest of the fermentation composition. Lack of mixing in dead zones results in depletion of the dissolved oxygen in the dead zone, which can lead to changes in microbial metabolism, metabolism rate, and/or microbial death. The recirculation loop 108 may eliminate these dead zones by drawing the fermentation composition out of the bottom 118 of the vessel 102 and returning the fermentation composition to the vessel 102.

As the fermentation process progresses, additional nutrient media may be added to the vessel 102 through at least one of the inlets 110 of the vessel 102. Nutrient media may be continuously added to the vessel 102 or may be added periodically to the vessel 102. At the start of an aerobic fermentation process, the volume of fermentation composition in the vessel 102 may be low, and the height H of the fermentation composition may be small such that only a portion of the vessel 102 has the fermentation composition in it. At this time, bubbles of oxygen-containing gas sparged into the vessel 102 by the aeration system 106 may not have sufficient contact time with the fermentation composition to achieve a mass transfer of oxygen to the fermentation composition to maintain aerobic conditions in the fermentation composition. These low volume conditions in the vessel 102 may extend through the first one third of the aerobic fermentation process. During these early stages of the aerobic fermentation process when the volume of fermentation composition in the vessel 102 is low, the recirculation loop 108 may provide the oxygen mass transfer rate sufficient to maintain aerobic conditions in the fermentation composition. Oxygen mass transfer using the recirculation loop 108 may also be advantageous during the early stages of the fermentation process during which periods of greater oxygen mass transfer rates may be needed to compensate for increased oxygen consumption through microbial metabolism. For example, high oxygen demand may occur during the early growth phase in which the microbial population increases. During the growth phase, oxygen consumption by the microorganisms increases necessitating greater oxygen mass transfer rates.

As the aerobic fermentation process progresses, nutrient media is added to the fermentation composition, thereby increasing the volume of the fermentation composition in the vessel 102 and the height H of the fermentation composition in the vessel 102. As the height H of the fermentation composition in the vessel 102 increases, the efficiency of oxygen mass transfer by the aeration system 106 increases. The height H of the fermentation composition in the vessel 102 may increase to a threshold height at which the oxygen mass transfer rate to the fermentation composition resulting from the aeration system 106 is sufficient to maintain aerobic conditions in the fermentation composition. At larger volumes of fermentation composition in the vessel 102, such as during the last approximately two-thirds of the aerobic fermentation process, the recirculation loop 108 may continue to provide additional mixing of the fermentation composition and heat transfer from the fermentation composition.

In some embodiments, the mass transfer rate of oxygen into the fermentation composition may be controlled during operation of the system 100 by controlling at least one of a flow rate of oxygen-containing gas introduced by the aeration system 106, a concentration of oxygen in the oxygen-containing gas introduced by the aeration system 106, a flow rate of oxygen-containing gas introduced to the eductor 140 of the recirculation system 108, the concentration of oxygen in the oxygen-containing gas introduced to the eductor 140 of the recirculation system 108, or a viscosity of the fermentation composition. In other embodiments, the mass transfer rate of oxygen into the fermentation composition may be controlled during operation of the system 100 by controlling the height of the fermentation composition in the vessel 102. In embodiments in which the vessel 102 is a pressure vessel, the mass transfer rate of oxygen into the fermentation composition may be controlled during operation of the system 100 by controlling a pressure in the vessel 102.

In embodiments, the fermentation composition may be passed through the recirculation loop 108 throughout the duration of the aerobic fermentation process. In some embodiments, the recirculation loop 108 may be operated during the aerobic fermentation process at least until the height H of fermentation composition in the vessel 102 reaches the threshold height at which a contact time of the bubbles of oxygen-containing gas from the aeration system 106 is sufficient to maintain the oxygen mass transfer rate into the fermentation composition that is equal to or greater than the uptake rate of oxygen in the fermentation composition due to microbial metabolism.

At the conclusion of the aerobic fermentation process, the fermentation composition may be removed from the vessel 102, and one or a plurality of fermentation compounds and/or products resulting from metabolism of the nutrient media by the microorganisms may be separated from the fermentation composition.

The system 100 having the combination of the aeration system 106 and the recirculation loop 108 may provide an oxygen mass transfer rate into the fermentation composition sufficient to maintain aerobic conditions in the fermentation composition in the vessel 102 throughout the fermentation process. In embodiments, the system 100 having the combination of the aeration system 106 and the recirculation loop 108 may provide an oxygen mass transfer rate sufficient to maintain aerobic conditions in the fermentation process without employing motorized agitation. In some embodiments, the system 100 having the combination of the aeration system 106 and the recirculation loop 108 may provide an oxygen mass transfer rate of from 10 millimoles per liter per hour (mmol/L/hr) to 150 mmol/L/hr. In embodiments, the system 100 having the combination of the aeration system 106 and the recirculation loop 108 may provide an oxygen mass transfer rate of from 10 mmol/L/hr to 120 mmol/L/hr, from 10 mmol/L/hr to 80 mmol/L/hr, from 10 mmol/L/hr to 50 mmol/L/hr, from 30 mmol/L/hr to 150 mmol/L/hr, from 30 mmol/L/hr to 120 mmol/L/hr, from 30 mmol/L/hr to 80 mmol/L/hr, from 50 mmol/L/hr to 150 mmol/L/hr, from 50 mmol/L/hr to 120 mmol/L/hr, from 50 mmol/L/hr to 80 mmol/L/hr, from 80 mmol/L/hr to 150 mmol/L/hr, or from 80 mmol/L/hr to 120 mmol/L/hr. In some embodiments, the system 100 having the combination of the aeration system 106 and the recirculation loop 108 may provide an oxygen mass transfer rate of up to 150 mmol/L/hr, or up to 120 mmol/L/hr, or up to 100 mmol/L/hr, or up to 80 mmol/L/hr.

The systems 100, 200 having the combination of the aeration system 106 and the recirculation loop 108 (and optionally the supplemental recirculation loop 208) enables greater capacity production of one or a plurality of products using aerobic fermentation compared to typical aerobic fermenters that do not have both the aeration system 106 and recirculation loop 108. The systems 100, 200 having the aeration system 106 and the recirculation loop 108 enables the use of larger volume tanks for the vessel 102, such as tanks having volumes of from 100 $m^3$ to 4000 $m^3$, for example. Additionally, the systems 100, 200 may enable the use of vessels 102 having smaller aspect ratios, such as aspect ratios of from 0.5 to 4 for example, compared to typical aerobic fermenters. The systems 100, 200 may also enable aerobic fermentation to be conducted at ambient pressures. Operating aerobic fermentation at ambient pressures enables the use of vessels 102 that are not pressure rated (e.g., non-pressurized tanks) and, thus, have thinner walls and are more cost effective compared to pressure vessels.

The aeration system 106 and the recirculation loop 108 of the system 100 provide uniform mixing of the fermentation composition in the vessel 102. Providing uniform mixing of the fermentation composition in the vessel 102 may eliminate the requirement for capital intensive motorized and/or mechanical agitation systems, which may require large motors greater than 3000 hp. In embodiments, the system 100 may be free of motorized and/or mechanical agitation and motorized/mechanical agitation systems Eliminating the requirement for motorized agitation systems may enable thin-walled vessels, such tanks complying with the American Petroleum Institute (API) standards for petroleum storage tanks for example, to be utilized as the vessel 102 of the system 100 for conducting greater-productivity aerobic fermentations. In embodiments, the vessel 102 of the system 100 may be a non-mechanically agitated vessel. The systems 100, 200 having the combination of the aeration system 106 and the recirculation loop 108 may also enable the retrofit of existing non-agitated vessels to conduct aerobic fermentation and may reduce the thickness of the vessels 102 specified for new aerobic fermentation facilities.

The combination of the aeration system 106 and recirculation loop 108 of the systems 100, 200 may provide oxygen mass transfer rates into the fermentation composition sufficient to maintain aerobic conditions in the fermentation composition over a wide range of liquid volumes in the vessel 102. This is particularly effective for fed-batch aerobic fermentation processes. During the initial growth phase (low liquid volume) of a fed-batch aerobic fermentation process, the efficiency of the aeration system 106 is expected to be small. During this initial growth phase, high oxygen mass transfer rates in the recirculation loop 108 provide the oxygen mass transfer sufficient to meet the dissolved oxygen demands and maintain aerobic conditions in the fermentation composition. As previously described, once the level of the fermentation composition in the vessel 102 is large enough, oxygen mass transfer using the recirculation loop 108 is expected to become less efficient due to increased turnover time of the fermentation composition. The turnover time is the time that it takes to circulate the equivalent of the entire volume of fermentation composition through the recirculation loop 108. Therefore, at greater volumes of fermentation composition in the vessel 102, the aeration system 106 provides greater and more efficient oxygen mass transfer to the fermentation composition compared to the recirculation loop 108.

The systems 100, 200 may provide an alternative for conducting fermentations with shear resistant microorganisms. Stirred fermenters having motorized agitation systems produce shear values of 3000 per second ($s^{-1}$) or greater, which is the same order of magnitude as the shear values expected from the static mixers 142. The static mixers 142, thus, may provide shear rates low enough to avoid causing damage to shear resistant microorganisms and avoid compromising the performance of the fermenter. Therefore, the systems, 100, 200 may provide a replacement for stirred fermentation systems.

Additionally, the systems 100, 200 having the aeration system 106 and recirculation loop 108 may provide possibility of having only the recirculation loop 108 as the source of oxygen mass transfer to the fermentation composition. Utilizing only the recirculation loop 108 to transfer oxygen to the fermentation composition may provide a fermentation environment conducive to conducting fermentation of facultative anaerobic or microaerophilic microorganisms. Facultative anaerobic bacteria can grow in the presence or in the absence of oxygen, but the presence of oxygen increases and may alter its metabolism. Some examples of facultative anaerobic bacteria may include, but are not limited to some species of *Lactobacillus, Bacillus, Streptococcus, Enterococcus*, or *Leuconstoc*, for example. Microaerophilic and strictly aerobic microorganisms cannot grow or ferment organic materials anaerobically. However, microaerophilic microorganisms may follow different metabolic pathways in the presence of high concentrations of oxygen. Examples of microaerophilic microorganisms may include, but are not limited to some species of *Escherichia, Klebsiellae, Streptomyces*, or *Propionibacterium*, for example. The systems 100, 200 disclosed herein may provide enhanced control of the oxygen mass transfer rate into the fermentation composition to conduct effective fermentations with these facultative anaerobic microorganisms or microaerophilic microorganisms.

The system 100 having the vessel 102, aeration system 106, and recirculation loop 108 as described herein can be employed in a method of conducting aerobic fermentation. A method for conducting aerobic fermentation includes introducing the fermentation composition to the vessel 102, sparging a first oxygen-containing gas stream into the fermentation composition, and passing a stream of the fermentation composition into the recirculation loop 108 comprising at least one eductor 140, at least one static mixer 142 downstream of the at least one eductor 140, and at least one heat exchanger 144 downstream of the at least one eductor 140. The first oxygen-containing stream may be sparged into the fermentation composition in the vessel 102 by the aeration system 106 having the compressor 122, sparger 120, and the optional air sterilizing system 132. The method of conducting aerobic fermentation further includes educting a second oxygen-containing gas stream into the stream of the fermentation composition with the at least one eductor 140 to produce a combined stream 160 comprising a liquid phase and a gas phase, wherein the liquid phase comprises the fermentation composition and the gas phase comprises the second oxygen-containing gas. The method further includes transferring oxygen from the gas phase to the liquid phase using the at least one static mixer 142 to produce an oxygenated fermentation composition 168. The method includes removing heat from the oxygenated fermentation composition 168 with the at least one heat exchanger 144 and passing the oxygenated fermentation composition 168 from the recirculation loop back to the vessel 102.

As previously discussed, in embodiments, the vessel 102 may have an aspect ratio of from 0.5 to 4, or from 0.5 to 2.0. The aspect ratio of the vessel 102 is defined as the height of the fermentation composition in the vessel 102 divided by the diameter of the vessel. In some embodiments, the internal volume of the vessel may be from 100 cubic meters ($m^3$) to 4000 $m^3$, or from 500 $m^3$ to 2000 $m^3$. The vessel 102 may include any feature or property according to an embodiment previously described in this disclosure.

In embodiments, the method may further include educting a third oxygen-containing gas stream into the oxygenated fermentation composition downstream of the at least one static mixer 142 and the at least one heat exchanger 144. In embodiments, the at least one static mixer 142 may be disposed within the at least one heat exchanger 144. In some embodiments, the fermentation composition may include a cell culture and a nutrient media. The system 100, including the vessel 102, aeration system 106, recirculation loop 108, and components thereof, may have any of the features and/or properties according to any embodiments previously described in this disclosure.

The systems 100, 200 for conducting aerobic fermentations may also be employed in a method for efficiently retrofitting or converting an anaerobic fermenter to an aerobic fermenter. For example, the aeration system 106, the recirculation system 108, or both may be fluidly coupled to the vessel of an existing anaerobic fermenter to convert the anaerobic fermenter to the system 100, 200 for converting aerobic fermentations. Conversion of existing anaerobic fermenters to the systems 100, 200 for conducting aerobic fermentations may be more efficient and cost effective than constructing new aerobic fermentation systems. Referring to FIG. 1, a method for converting an anaerobic fermenter to a system 100 for conducting aerobic fermentation includes fluidly coupling an aeration system 106 to a vessel 102 of the anaerobic fermenter, wherein the aeration system 106 includes a sparger 120 fluidly coupled to the vessel 102 and positioned to introduce a compressed gas to an internal volume of the vessel 102. The method further includes fluidly coupling a recirculation loop 108 to an outlet 104 of the vessel 102. The recirculation loop 108 includes an eductor 140, at least one static mixer 142 positioned downstream of the eductor 140, at least one heat exchanger 144 positioned downstream of the eductor 140, and at least one distributor 146 positioned downstream of the at least one static mixer 142 and the at least one heat exchanger 144. The distributor 146 may be fluidly coupled to the internal volume of the vessel 102. The recirculation loop 108 may also include a pump 170 for circulating the fermentation composition through the recirculation loop 108.

EXAMPLES

The following Examples are presented for demonstrating the performance of various aspects of the systems 100, 200 described in this disclosure.

Example 1

Oxygen Mass Transfer by Aeration

Experiments were conducted to determine appropriate scale up criteria for delivering a volumetric mass transfer coefficient $k_L a$ of 0.1 per second ($s^{-1}$) within the entire vessel of the aerobic fermentation system. Experiments were conducted in an 1800 gallon vessel having an aeration system fluidly coupled to the vessel. The vessel had an internal diameter D of 66 inches and a straight side height $H_v$ of 120". The height H of the liquid within the vessel was changed by adding more liquid to the vessel or draining a portion of the existing contents. Experiments were performed over a range of liquid heights H from 3 feet to 8 feet corresponding to aspect ratios (H/D) in the range of 0.55 to 1.5. In each experiment, the liquid used was water at a nominal temperature of from 18° C. to 20° C. The air was introduced to the vessel through an air sparger having a nominal outside diameter of about 50 inches, and the flow rate of air was controlled using a pneumatically controlled flow valve. For each liquid height, the oxygen-containing gas was bubbled through the liquid by the aeration system at different aeration rates $\dot{Q}_g$ ranging from 20 standard cubic feet per minute (scfm) to 300 scfm. The oxygen concentration in the liquid C(t) was measured as a function of time for each experiment characterized by a different set of operating parameters (H, $\dot{Q}_g$). The volumetric mass transfer coefficient $k_{La}$ was then estimated from the C(t) measurements. This method is commonly referred to as the dynamic $k_L a$ measurement method. The oxygen concentration in the liquid C(t) was measured using a ProODO model dissolved oxygen (DO) meter marketed by YSI, Inc. The probe of the DO meter had a response delay, $\tau_P$=9 seconds. This delay was accounted for in estimating the $k_{La}$ from the temporal measurements of the dissolved oxygen. For each experiment at each liquid height and aeration rate (H, $\dot{Q}_g$), a non-dimensional criterion, namely oxygen transfer efficiency $\eta_s$, was deduced from the experiments. The following Equation 2 was used to calculate the oxygen transfer efficiency:

$$\eta_s(\%) = \frac{k_L a}{\dot{Q}_g / V_l} \times \frac{\Delta C}{\rho_{o_2}} \times 100 \qquad \text{Equation 2}$$

where $\dot{Q}_g$ is the aeration rate (standard cubic meters of gas per second (std m³/s)) of the gas into the liquid in the vessel, $V_l$ is the liquid volume in cubic meter (m³), $\rho_{o_2}$ is the weight in kilograms of oxygen ($O_2$) per standard cubic meter of air (kgO₂/std-m³-air), and $\Delta C$ is the change in concentration of oxygen in the fermentation composition liquid in units of kilograms of oxygen ($O_2$) per cubic meter of the fermentation composition (broth) (kgO₂/m³-broth). The oxygen transfer efficiency $\eta_s$ is reported herein in units of percent (%).

Figure 5:
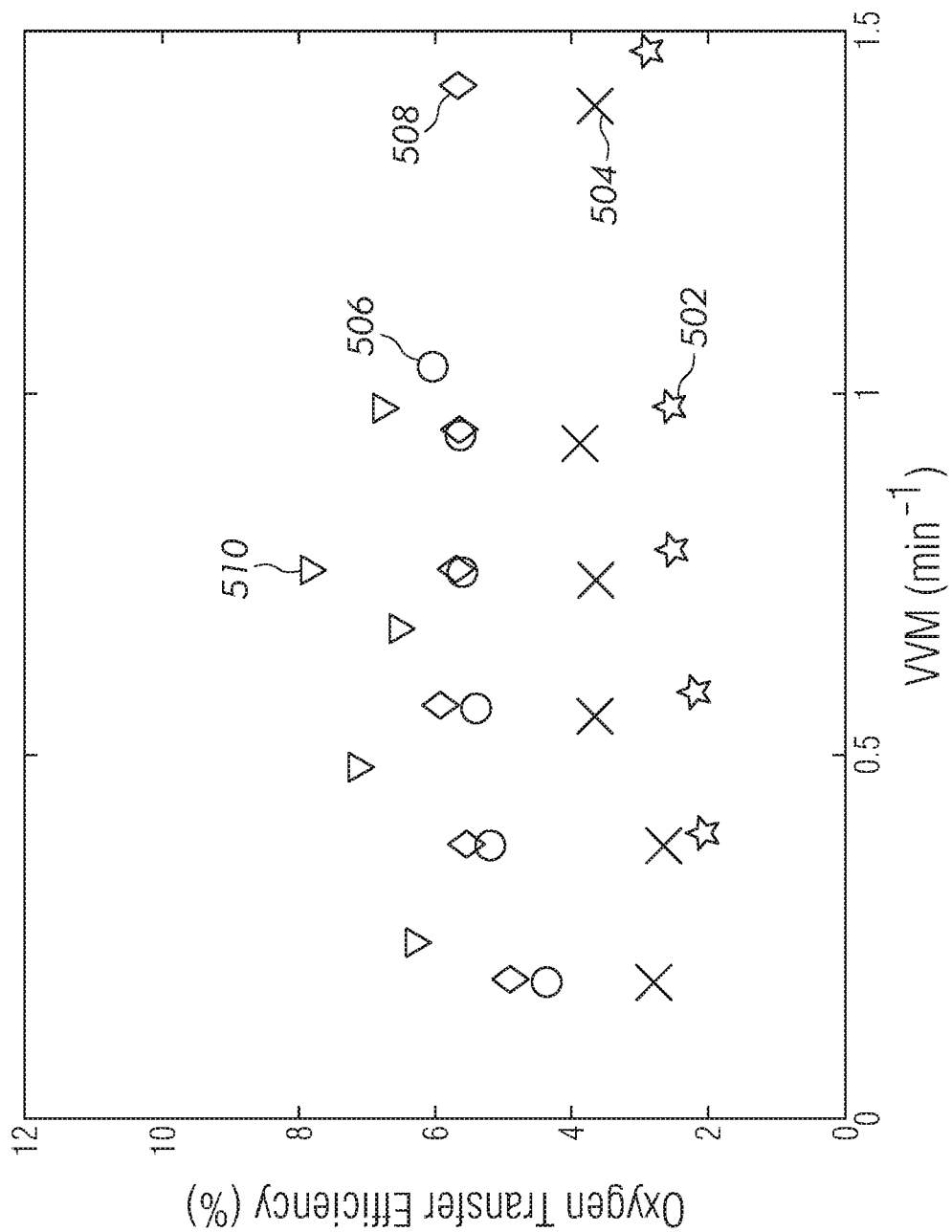
FIG. 5 is a plot of the oxygen transfer efficiency as a function of the volume flow rate of gas per minute, per unit liquid volume (VVM) for an aeration system of the system for conducting aerobic fermentation of FIG. 1 independent of operation of a recirculation loop of the system, in accordance with one or more embodiments of the present disclosure.

Referring now to FIG. 5, the oxygen transfer efficiency $\eta_s$ is plotted against the specific gassing rate (i.e., volume flow rate of gas per minute, per unit liquid volume (VVM)) for each of the different liquid heights. The specific gassing rate VVM was calculated from Equation 3:

$$VVM = 60 \times \frac{\dot{Q}_g}{V_l} \qquad \text{Equation 3}$$

where VVM is in units of per minute ($min^{-1}$). Series 502 represents the oxygen transfer rate $\eta_s$ at a liquid height of 3 feet at various aeration rates $\dot{Q}_g$. Series 504 represents the oxygen transfer rate $\eta_s$ at a liquid height of 4 feet at various aeration rates $\dot{Q}_g$. Series 506 represents the oxygen transfer rate $\eta_s$ at a liquid height of 6 feet at various aeration rates $\dot{Q}_g$. Series 508 represents the oxygen transfer rate $\eta_s$ at a liquid height of 7 feet at various aeration rates $\dot{Q}_g$. Series 510 represents the oxygen transfer rate $\eta_s$ at a liquid height of 8 feet at various aeration rates $\dot{Q}_g$.

As shown in FIG. 5, at each height, the oxygen transfer efficiency $\eta_s$ into the liquid is relatively insensitive to changes in VVM, as indicated by the lack of substantial change in the oxygen transfer efficiency $\eta_s$ with increasing VVM. This indicates that the oxygen transfer efficiency $\eta_s$ is relatively insensitive to changes in the aeration rate $\dot{Q}_g$. However, oxygen transfer efficiency $\eta_s$ increases with increasing liquid height from about 2% at the height of 3 feet of series 502 to about 7% at the height of 12 feet 510.

Figure 6:
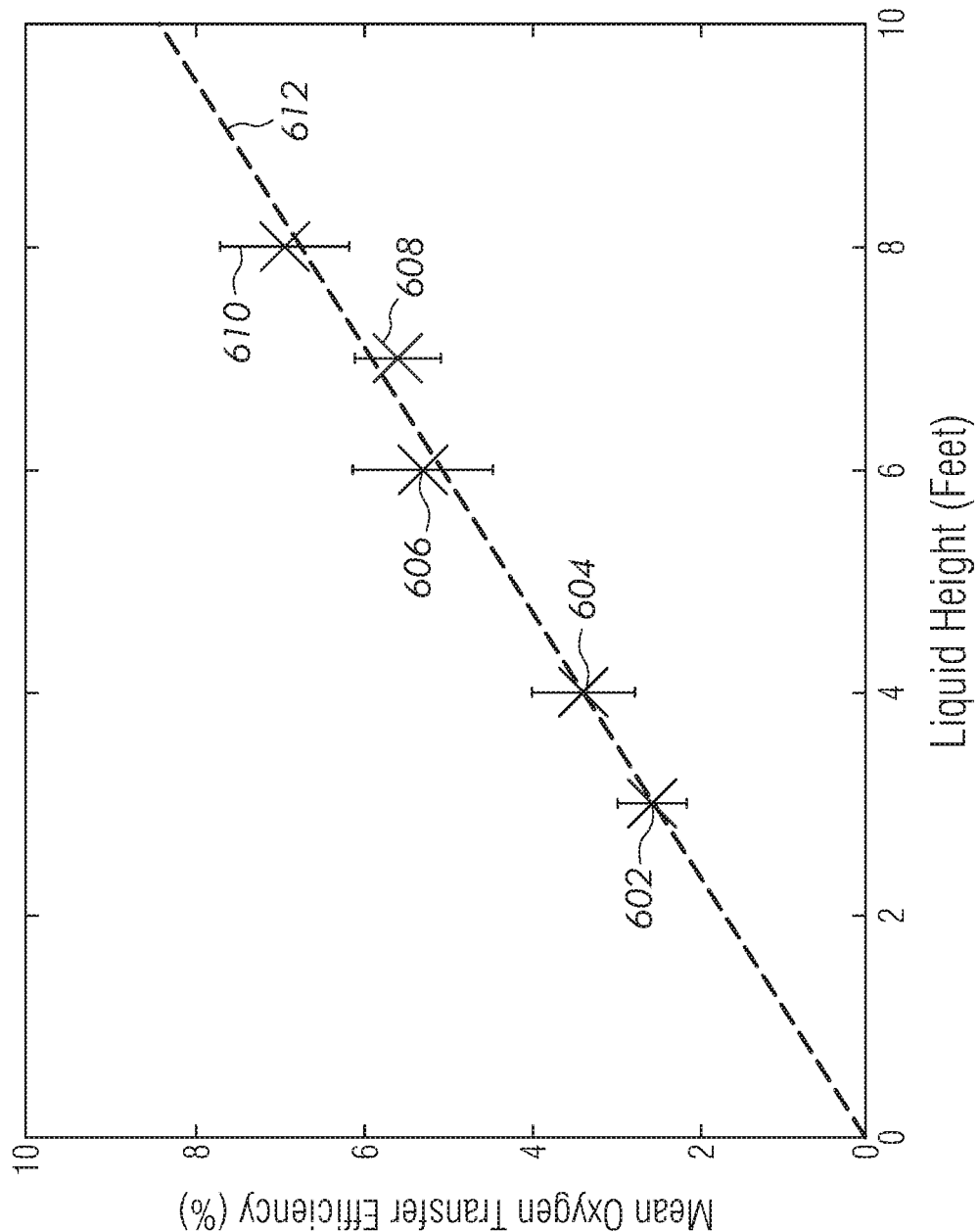
FIG. 6 is a plot of the mean oxygen transfer efficiency as a function of liquid height for an aeration system of the system for conducting aerobic fermentation of FIG. 1 independent of operation of a recirculation loop of the system, in accordance with one or more embodiments of the present disclosure.

Referring now to FIG. 6, the mean oxygen transfer efficiency $\eta_{s,mean}$ is plotted against the liquid height H in feet. The mean oxygen transfer efficiency at each height H was determined using the following Equation 4:

$$\eta_{s,mean} = \left(\frac{1}{n}\right) \sum_n \eta_{s,n} (\dot{Q}_{g,n}, H) \qquad \text{Equation 4}$$

where n is the number of data points collected at each specific liquid height H (in this Example, n is equal to 6), and $\eta_{s,n}$ is the oxygen transfer efficiency at each data point for each specific liquid height H. As shown in FIG. 6, the mean oxygen transfer efficiency $\eta_{s,mean}$ increases almost linearly with increasing liquid height H from a liquid height of 3 feet 602 to 4 feet 604, 6 feet 606, 7 feet 608, and 8 feet 610. A trend line 612 fit to the data in FIG. 6 exhibits a slope of about 0.85% per foot indicating that a one foot increase in liquid height H produces about a 0.85% increase in mean oxygen transfer efficiency $\eta_{s,mean}$.

With this understanding, a production-scale oxygen transfer efficiency may be from 10% to 40%. Applying this range of oxygen transfer efficiencies, an aeration flow rate $\dot{Q}_g$ sufficient to provide a specific overall volumetric mass transfer coefficient $k_L a$ may be estimated using the following Equation 4:

$$\dot{Q} \approx \frac{\Delta C}{\rho_{O_2}} \times \frac{k_L a \times V_l}{\eta_s} \qquad \text{Equation 5}$$

where $\eta_s$ can be estimated from FIG. 6, $k_L a$ is the volumetric mass transfer coefficient and is a part of process specification, $V_l$ is the liquid volume, $\Delta C$ is 0.0085 kilograms of oxygen ($O_2$) per cubic meter of the fermentation composition (broth) (kg$O_2$/m$^3$-broth), and $\rho_{O_2}$ is approximately equal to 0.28 kilograms of oxygen ($O_2$) per standard cubic meter of air (kg$O_2$/std-m$^3$-air). A 50% safety factor on the estimated $\dot{Q}_g$ is recommended to account for uncertainties in operating conditions (e.g. viscosity, temperature, broth composition, etc.). As an example, an aeration rate $\dot{Q}_g$ at the production scale of 2000 m$^3$ is expected to be in a range from 20,000 scfm to 80,000 scfm in order to deliver an oxygen mass transfer rate in the range of from 0.02 s$^{-1}$ to 0.12 s$^{-1}$.

Example 2

Oxygen Mass Transfer in Recirculation Loop Having Static Mixers

Increasing the oxygen mass transfer rate by circulating the fermentation composition through the recirculation loop 108 may provide improved performance during certain stages of the aerobic fermentation process. As an example, such a situation occurs during the growth phase of microbial population (microorganism), when much greater oxygen mass transfer rates are needed to maintain the oxygen mass transfer rate at a level equal to or greater than the consumption of dissolved oxygen through microbial metabolism compared to regular operation of the aerobic fermentation process. As previously discussed herein, limiting the length of the recirculation may reduce fouling of the surfaces of the recirculation loop. This means a shorter residence time for the fermentation composition in the recirculation loop. Therefore, the recirculation may be designed to provide greater oxygen transfer rates compared to the aeration system.

Figure 7:
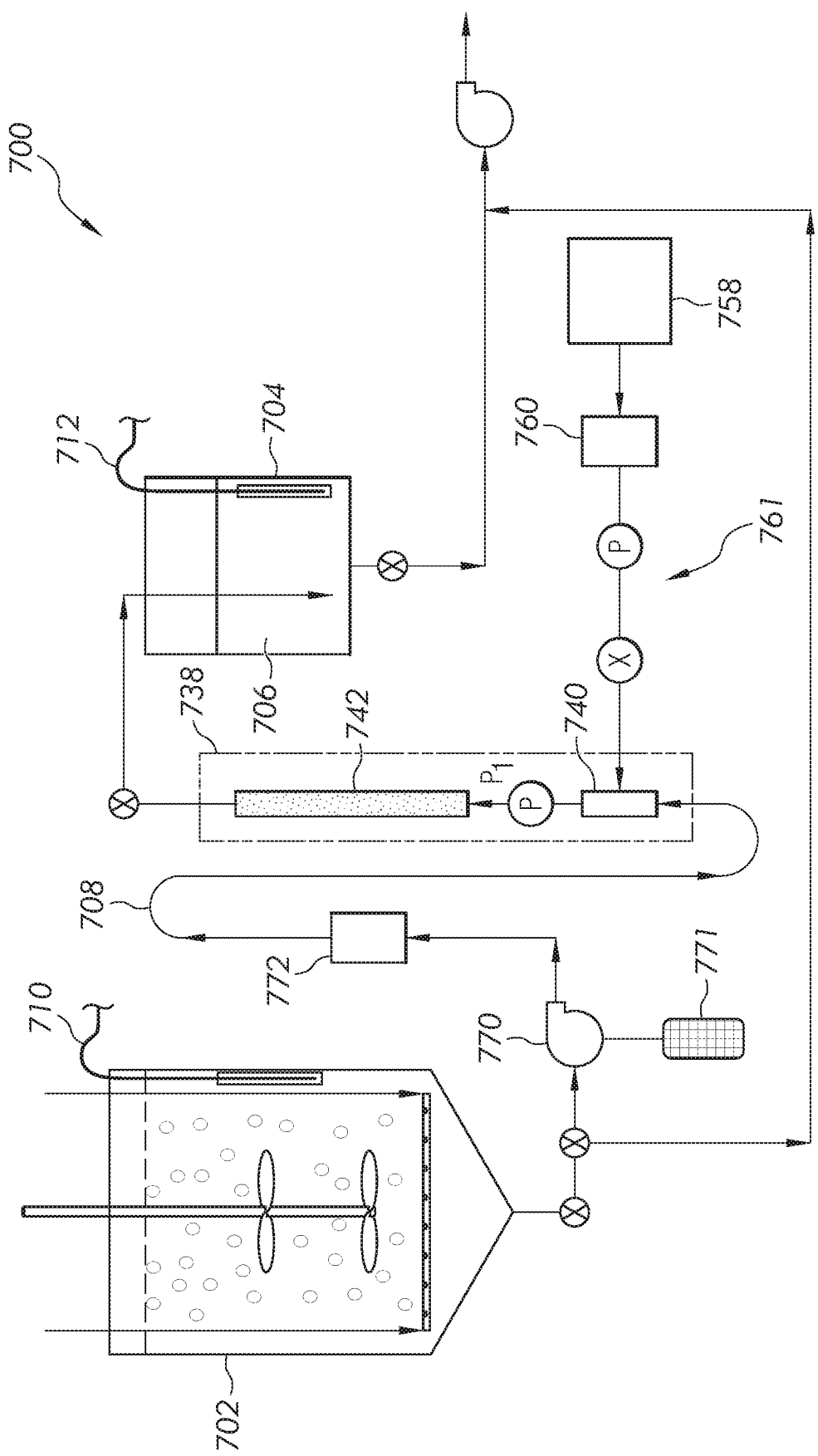
FIG. 7 schematically depicts a laboratory apparatus for evaluating the oxygen transfer efficiency of a recirculation loop in Example 2, in accordance with one or more embodiments of the present disclosure.

Experiments were performed to demonstrate the feasibility of obtaining greater oxygen transfer rates using a recirculation loop having an eductor and a static mixer. Referring to FIG. 7, the laboratory apparatus 700 used for conducting the experiments consisted of a first hold tank 702, a centrifugal pump 770 operated with a variable frequency drive (VFD) 771, a flow meter 772 to measure the liquid flow rate supplied to the eductor-static mixer assembly 738, and a flow line 761 for air. The air flow rate was measured using a rotameter 760. The eductor-static mixer assembly 738 included an eductor 740 and a static mixer 742 positioned downstream of the eductor 740. The static mixer was a nominal 1 inch SMX™ static mixer manufactured by Sulzer Ltd. The gas-liquid two phase flow emerging from the eductor-static mixer assembly 738 was collected in a second hold tank 704, where the air bubbles disengaged from the liquid, leaving behind the oxygenated water 706. A first DO meter 710 was positioned in the first hold tank to measure the dissolved oxygen level in the first hold tank 702, and a second DO meter 712 was position in the second hold tank 704 to measure the dissolved oxygen level in of the oxygenated water 706 in the second hold tank 704. The first DO meter 710 and the second DO meter 712 were both ProODO model DO meters marketed by YSI, Inc. The dissolved oxygen level in the first hold tank 702 was recorded as $C_i$ and the dissolved oxygen level in the second hold tank 704 was recorded as $C_o$. Experiments were conducted at multiple liquid flow rates $\dot{Q}_l$ through the contactor ranging from 2 gallons per minute (gpm) to 10 gpm. For each liquid flow rate $\dot{Q}_l$, the air flow rate $\dot{Q}_g$ was varied such that the flow rate ratio was in the range of from 0.05 to 1. For each experiment, the $k_L a$ value was estimated using Equation 6:

$$k_L a = \frac{\dot{Q}_g + \dot{Q}_l}{\frac{\pi}{4} D_{pipe}^2 L_{pipe}} \times \ln\left(1 - \frac{C_i}{C_o}\right), \qquad \text{Equation 6}$$

Where $D_{pipe}$ is the inner diameter of the pipe of the eductor-static mixer assembly 738 and is equal to 1.04 inches, and $L_{pipe}$ is the length of the pipe extending from the eductor 740 to the second hold tank 704 and is equal to 40 inches.

Figure 8A:
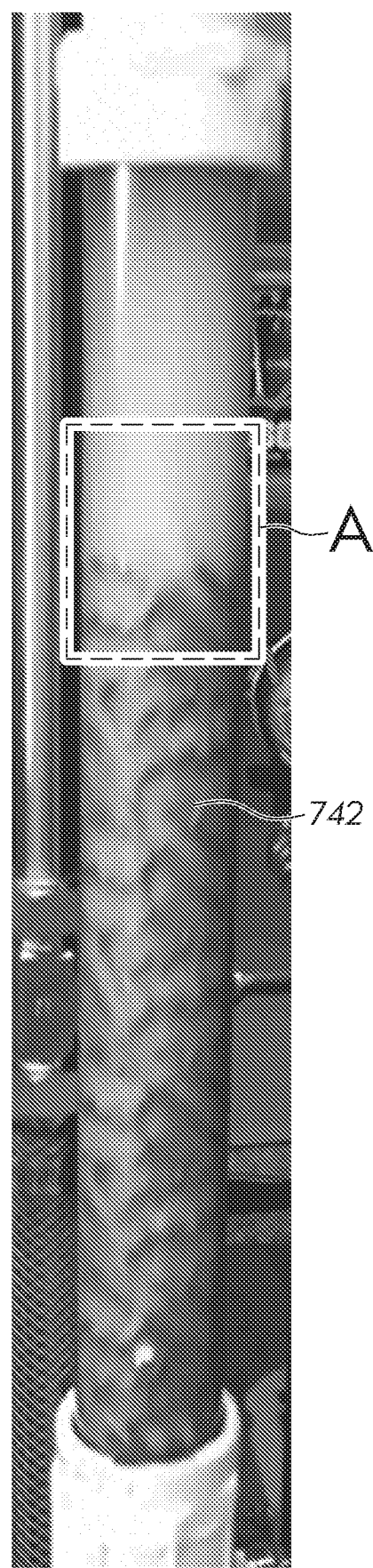
FIG. 8A is a photograph of a static mixer of the laboratory apparatus of FIG. 7, in accordance with one or more embodiments of the present disclosure.
Figure 8B:
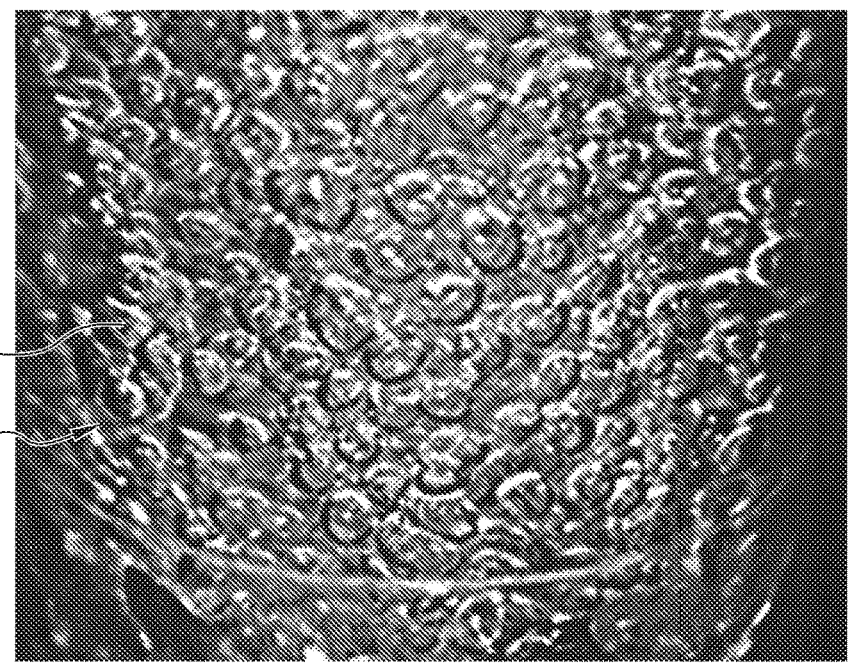
FIG. 8B is a is a photograph of fluid flow through the static mixer of FIG. 8A at flow rate of 2 gallons per minute, in accordance with one or more embodiments of the present disclosure.
Figure 8C:
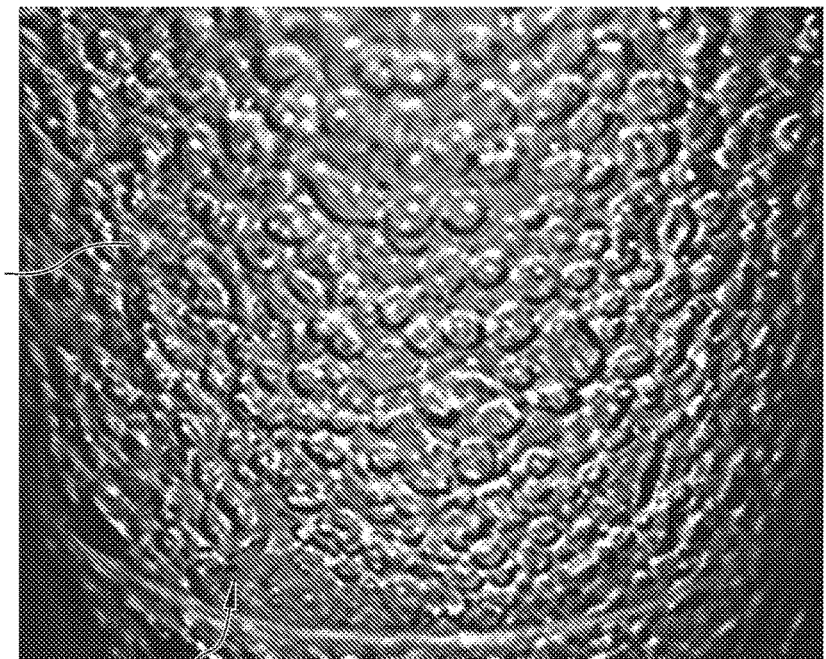
FIG. 8C is a photograph of fluid flow through the static mixer of FIG. 8A at flow rate of 4 gallons per minute, in accordance with one or more embodiments of the present disclosure.
Figure 8D:
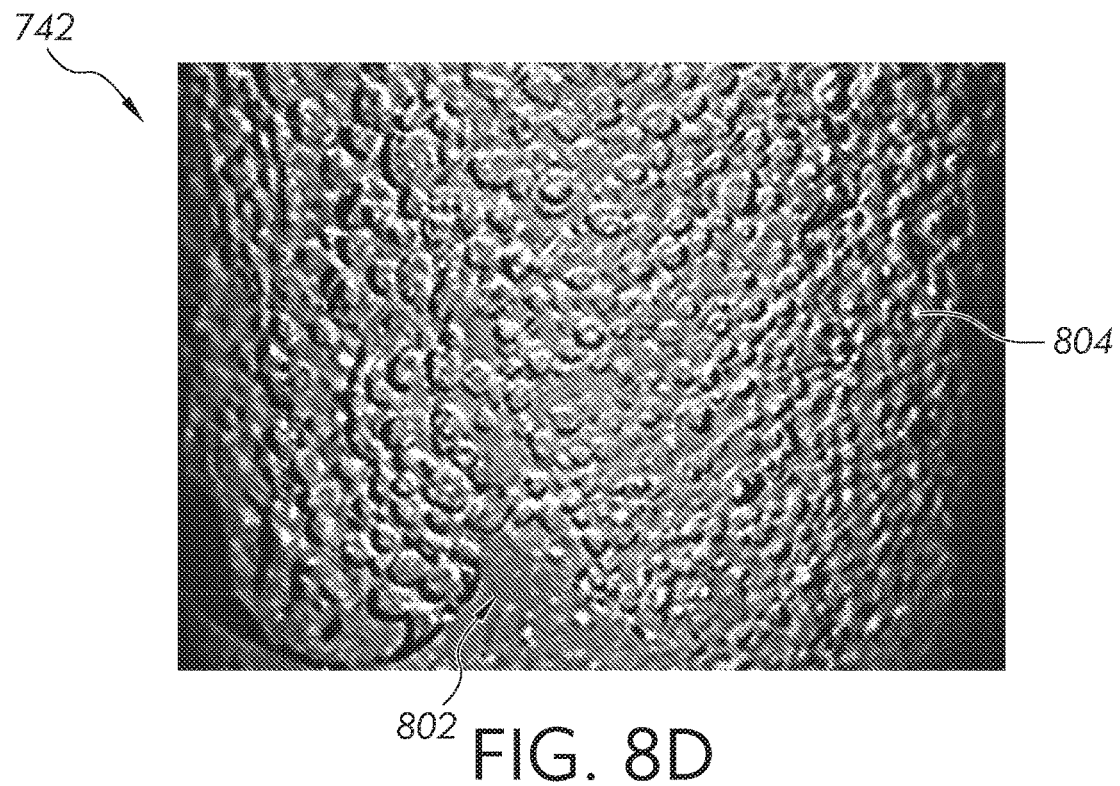
FIG. 8D is a photograph of fluid flow through the static mixer of FIG. 8A at flow rate of 6 gallons per minute, in accordance with one or more embodiments of the present disclosure.
Figure 8E:
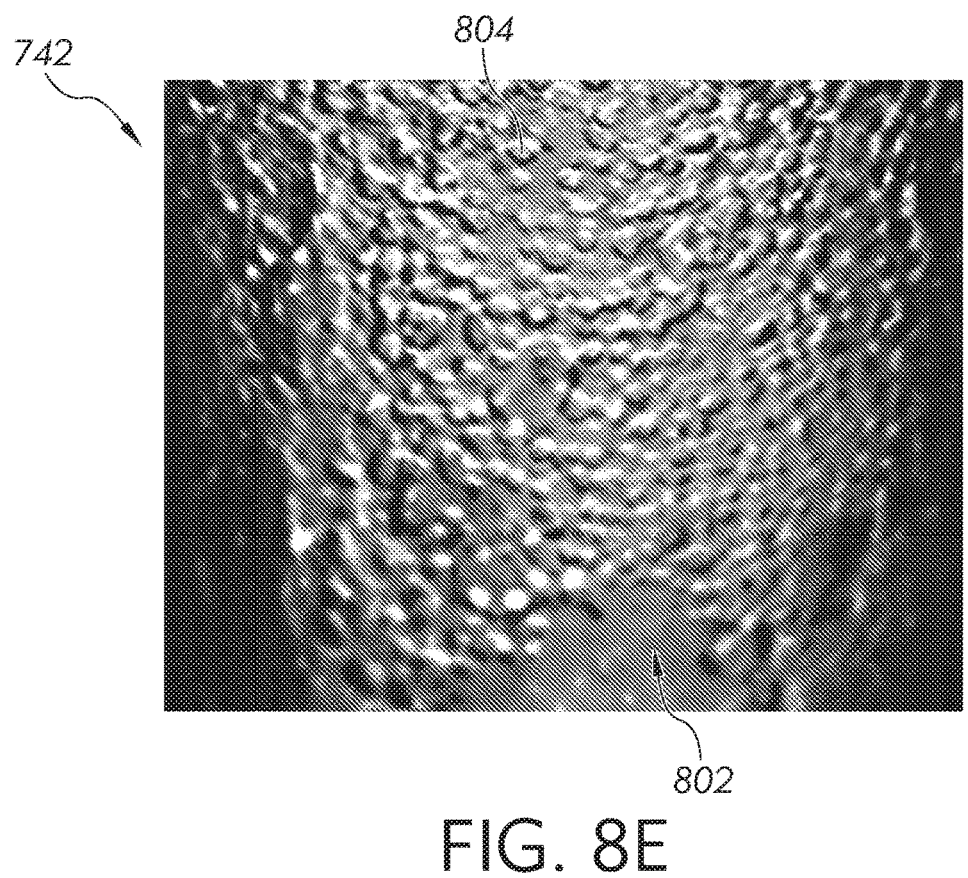
FIG. 8E is a photograph of fluid flow through the static mixer of FIG. 8A at flow rate of 8 gallons per minute, in accordance with one or more embodiments of the present disclosure.

FIG. 8A is a photograph of the static mixer 742 of the laboratory apparatus 700 of Example 2. The static mixer 742 was positioned inside of a transparent conduit to enable visual inspection and imaging of the flow through the static mixer 742. FIGS. 8B-8E are photographs of the flow of the liquid 802 and air bubbles 804 through the static mixer 742 taken at region A of FIG. 8A. The ratio of the gas flow rate to the liquid flow rate was constant at 0.8 for each of FIGS. 8B-8E. The total flow rate for FIG. 8B was 2 gallons per minute (gpm), the total flow rate for FIG. 8C was 4 gpm, the total flow rate for FIG. 8D was 6 gpm, and the total flow rate for FIG. 8E was 8 gpm. As shown in FIGS. 8B-8E, the average size of the gas bubbles created by the static mixer 742 decrease as the total flow rate through the static mixer 742 increases.

Figure 9:
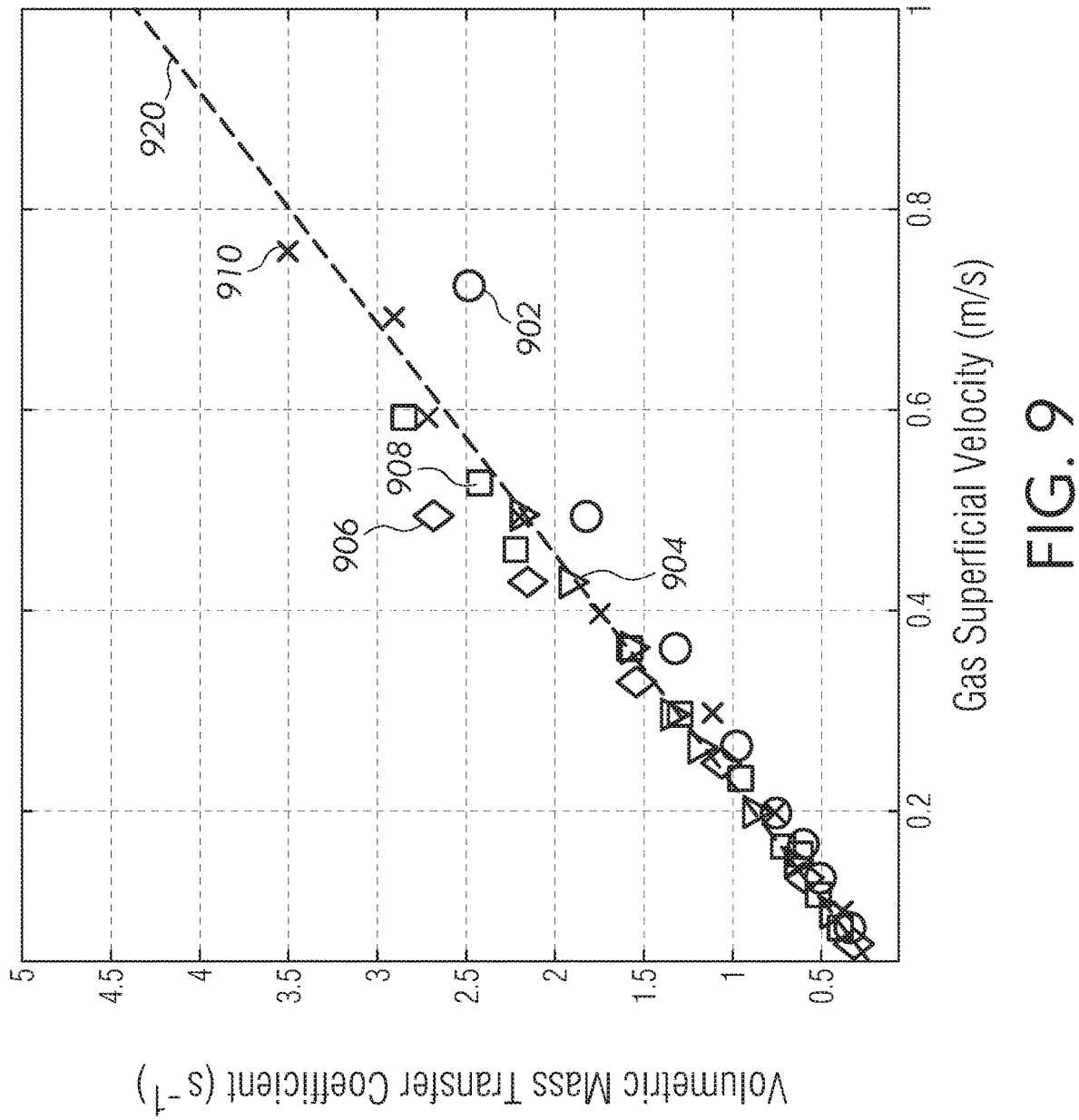
FIG. 9 is a plot of the volumetric mass transfer coefficient as a function of space velocity through a static mixer in a recirculation loop of the system for conducting aerobic fermentation of FIG. 1, in accordance with one or more embodiments of the present disclosure.

One consideration in sizing production equipment is ensuring turbulent flow everywhere within the static mixer. FIG. 9 shows the volumetric mass transfer coefficient $k_L a$ values obtained within the recirculation loop over a range of liquid flow rates $\dot{Q}_l$ and gas flow rates $\dot{Q}_g$ plotted as a function of the gas superficial velocity $U_g$ (m/s) through the eductor-static mixer assembly 738, which is calculated using Equation 7:

$$U_g = \frac{4\dot{Q}_g}{\pi D_{pipe}^2} \qquad \text{Equation 7}$$

where $\dot{Q}_g$ is the gas flow rate and $D_{pipe}$ is the inner diameter of the pipe of the eductor-static mixer assembly 738 and is equal to 1.04 inches. In FIG. 9, data series 902 was obtained at a liquid flow rate of 2 gallons per minute (gpm), data series 904 was obtained at a liquid flow rate of 4 gpm, the data series 906 was obtained at a liquid flow rate of 5 gpm, data series 908 was obtained at a liquid flow rate of 6 gpm, and data series 910 was obtained at a liquid flow rate of 8 gpm. As shown in FIG. 7, increasing the gas superficial velocity $U_g$ through the static mixer 742 increases the volumetric mass transfer coefficient $k_L a$. As shown by the trendline 920 in FIG. 9, the relationship between the gas superficial velocity $U_g$ through the static mixer 742 and the volumetric mass transfer coefficient $k_L a$ is generally linear. The slope of the trendline 920 in FIG. 9 is 4.3 minutes$^{-1}$. However, the slope of the trendline 920 is likely to depend upon the type of static mixer 742 used (SMX in the present case), and details of the eductor geometry. The slope is largely insensitive to gas and liquid flow rates.

As shown in FIG. 9, the volumetric mass transfer coefficients $k_L a$ measured for the recirculation loop in Example 2 are from 5 to 30 times greater than the volumetric mass transfer coefficient $k_L a$ for the aeration system of Example 1.

Throughout this disclosure ranges are provided for various parameters and characteristics of system 100 for conducting aerobic fermentations. It will be appreciated that when one or more explicit ranges are provided, the individual values and the ranges formed therebetween are also intended to be provided, as providing an explicit listing of all possible combinations is prohibitive. For example, a provided range of 1-10 also includes the individual values, such as 1, 2, 3, 4.2, and 6.8, as well as all the ranges which may be formed within the provided bounds, such as 1-8, 2-4, 6-9, and 1.3-5.6.

It should now be understood that various aspects of the system 100 for conducting aerobic fermentation and methods of conducting aerobic fermentation using the system 100 are described and such aspects may be utilized in conjunction with various other aspects. It should also be understood to those skilled in the art that various modifications and variations can be made to the described embodiments without departing from the spirit and scope of the claimed subject matter. Thus, it is intended that the specification covers the modifications and variations of the various described embodiments provided such modifications and variations come within the scope of the appended claims and their equivalents.

The invention claimed is:

1. A system for aerobic fermentation comprising:
a vessel;
an aeration system comprising a gas sparger fluidly coupled to the vessel and positioned to introduce a compressed gas to an internal volume of the vessel;
an oxygen-containing gas source; and
a recirculation loop fluidly coupled to an outlet of the vessel, the recirculation loop comprising:
at least one eductor fluidly coupled to the oxygen-containing gas source;
at least one static mixer downstream of the at least one eductor;
at least one heat exchanger downstream of the at least one eductor; and
at least one distributor downstream of the at least one static mixer and the at least one heat exchanger, the at least one distributor fluidly coupled to the internal volume of the vessel;
wherein when a fermentation composition is introduced to the vessel, the gas sparger and the recirculation loop provide mixing to the fermentation composition, and a stream of the fermentation composition passes from the vessel into the recirculation loop, through the at least one eductor, the at least one static mixer, and the at least one heat exchanger of the recirculation loop, and passes out of the at least one distributor back into the internal volume of the vessel.

2. The system of claim 1, wherein the vessel has a maximum aspect ratio of from 0.5 to 4, the maximum aspect ratio of the vessel defined as the maximum height of the fermentation composition in the vessel divided by the diameter of the vessel, and wherein the internal volume of the vessel is from 100 cubic meters (m$^3$) to 4000 m$^3$.

3. The system of claim 1, wherein the recirculation loop further comprises a pump fluidly coupled to the recirculation loop, wherein when the fermentation composition is introduced to the vessel, the pump circulates the stream of fermentation composition through the recirculation loop.

4. The system of claim 1, wherein the at least one static mixer is positioned within the at least one heat exchanger.

5. The system of claim 1, wherein the at least one heat exchanger comprises a shell-and-tube heat exchanger, a plate-and-frame heat exchanger, or both.

6. The system of claim 1, wherein the distributor is positioned within the interior volume of the vessel.

7. The system of claim 1, wherein the aeration system comprises at least one compressor fluidly coupled to the gas sparger.

8. The system of claim 7, wherein the aeration system further comprises an air sterilization apparatus fluidly coupled to the compressor or the gas sparger.

9. The system of claim 1, wherein the recirculation loop comprises a first eductor and a second eductor, wherein the first eductor is positioned upstream of the at least one heat exchanger and the at least one static mixer and the second eductor is positioned downstream of the at least one heat exchanger and the at least one static mixer.

10. The system of claim 1, wherein the recirculation loop comprises at least one first heat exchanger and at least one second heat exchanger, wherein the at least one first heat exchanger is positioned upstream of the at least one eductor, and the at least one second heat exchanger is positioned downstream of the at least one eductor.

11. The system of claim 1, further comprising at least one supplemental recirculation loop comprising an eductor, a heat exchanger, and a static mixer.

12. The system of claim 1, wherein the vessel has a maximum aspect ratio from 0.5 to 2.0, the maximum aspect ratio of the vessel defined as the maximum height of the fermentation composition in the vessel divided by the diameter of the vessel, and wherein the internal volume of the vessel is from 500 cubic meters (m$^3$) to 2000 m$^3$.

13. A method for conducting aerobic fermentation, the method comprising:
introducing a fermentation composition to the vessel of the system of claim 1;
sparging a first oxygen-containing gas stream into the fermentation composition;
passing a stream of the fermentation composition into the recirculation loop;
educting a second oxygen-containing gas stream into the stream of the fermentation composition with the at least one eductor to produce a combined stream comprising a liquid phase and a gas phase, wherein the liquid phase comprises the fermentation composition and the gas phase comprises the second oxygen-containing gas;
transferring oxygen from the gas phase to the liquid phase using the at least one static mixer to produce an oxygenated fermentation composition in the liquid phase;
removing heat from the oxygenated fermentation composition using the at least one heat exchanger; and
passing the oxygenated fermentation composition from the recirculation loop back to the vessel.

14. The method of claim 13, wherein the vessel has a maximum aspect ratio of from 0.5 to 4, the maximum aspect ratio of the vessel defined as the maximum height of the fermentation composition in the vessel divided by the diameter of the vessel, and wherein the internal volume of the vessel is from 100 cubic meters ($m^3$) to 4000 $m^3$.

15. The method of claim 13, further comprising educting a third oxygen-containing gas stream into the oxygenated fermentation composition downstream of the at least one static mixer and the at least one heat exchanger.

16. The method of claim 13, wherein the fermentation composition comprises a cell culture and a nutrient media.

17. The method of claim 13, wherein the vessel has a maximum aspect ratio of from 0.5 to 2.0, the maximum aspect ratio of the vessel defined as the maximum height of the fermentation composition in the vessel divided by the diameter of the vessel, and wherein the internal volume of the vessel is from 500 cubic meters ($m^3$) to 2000 $m^3$.

* * * * *